United States Patent
Horvath et al.

(10) Patent No.: US 11,571,506 B2
(45) Date of Patent: Feb. 7, 2023

(54) STERILE SEALED HETEROGENEOUS MEDICAMENT DELIVERY DEVICE

(71) Applicant: Genentech, Inc., South San Fransisco, CA (US)

(72) Inventors: Joshua Horvath, San Ramon, CA (US); Lionel Vedrine, San Mateo, CA (US); Nathan A. Goltz, Oceanside, CA (US); Mukund R. Patel, San Jose, CA (US); Aaron D. Chesterman, Fremont, CA (US); Mayumi Naito Bowen, El Cerrito, CA (US)

(73) Assignee: Genentech, Inc., South San Francisco, CA (US)

( * ) Notice: Subject to any disclaimer, the term of this patent is extended or adjusted under 35 U.S.C. 154(b) by 575 days.

(21) Appl. No.: 16/384,410

(22) Filed: Apr. 15, 2019

(65) Prior Publication Data

US 2019/0240394 A1 Aug. 8, 2019

Related U.S. Application Data

(63) Continuation of application No. PCT/US2017/057525, filed on Oct. 20, 2017.
(Continued)

(51) Int. Cl.
*A61M 5/00* (2006.01)
*A61L 2/08* (2006.01)
(Continued)

(52) U.S. Cl.
CPC ............. *A61M 5/001* (2013.01); *A61L 2/08* (2013.01); *A61L 2/087* (2013.01); *A61L 31/048* (2013.01);
(Continued)

(58) Field of Classification Search
CPC .... A61M 5/001; A61M 5/1785; A61M 5/002; A61M 5/2033; A61M 2205/0272;
(Continued)

(56) References Cited

U.S. PATENT DOCUMENTS 3,359,125 A * 12/1967 Bishop ............... G01T 1/06
501/64
4,652,763 A 3/1987 Nablo
(Continued)

FOREIGN PATENT DOCUMENTS

CN 102464145 5/2012
CN 104470557 3/2015
(Continued)

OTHER PUBLICATIONS

English Translation of Office Action received from Chinese Patent Office in connection with Chinese Application No. 201780064821.3, dated Jan. 22, 2021.
(Continued)

*Primary Examiner* — Kevin C Sirmons
*Assistant Examiner* — Avery Smale
(74) *Attorney, Agent, or Firm* — Weiss & Arons LLP

(57) ABSTRACT

Apparatus and methods for delivering medicament to a patient. The apparatus may include elements with different capacities to attenuate or absorb sterilizing radiation. The apparatus may include a medicament delivery assembly with interactive elements for dose-setting, priming and medicament ejection. The assembly may include a chamber housing a radiation-sensitive medicament present in the apparatus during sterilization by electron beam. The assembly may include an actuator chassis, a drive mechanism, a needle-priming mechanism and a fluid-displacement mechanism including a fluid-displacement member. The chassis may be fixed, relative to an outlet, to the chamber. The member may
(Continued)

be slidingly and/or threadingly engaged with the chassis, and may be configured to move relative to the outlet to deliver the medicament through the outlet. Assembly elements may be nested coaxially and/or stacked axially. The assembly may include at least one hollow region. The hollow region may reduce beam attenuation or reduce radiation absorption.

124 Claims, 17 Drawing Sheets

Related U.S. Application Data

(60) Provisional application No. 62/411,182, filed on Oct. 21, 2016.

(51) Int. Cl.
| | | |
|---|---|---|
| *A61M 5/178* | (2006.01) | |
| *A61M 5/145* | (2006.01) | |
| *A61M 5/20* | (2006.01) | |
| *A61M 5/315* | (2006.01) | |
| *A61L 31/04* | (2006.01) | |

(52) U.S. Cl.
CPC ........ *A61M 5/002* (2013.01); *A61M 5/14586* (2013.01); *A61M 5/1785* (2013.01); *A61M 5/2033* (2013.01); *A61L 2202/14* (2013.01); *A61L 2202/181* (2013.01); *A61L 2202/24* (2013.01); *A61M 2005/31588* (2013.01); *A61M 2202/0413* (2013.01); *A61M 2202/0486* (2013.01); *A61M 2202/09* (2013.01); *A61M 2205/0272* (2013.01)

(58) Field of Classification Search
CPC ............ A61M 2205/0283; A61M 5/20; A61M 5/14586; A61M 2005/31588; A61M 2202/0413; A61M 2202/0486; A61M 2202/09; A61L 2/08; A61L 2/087; A61L 2202/14; A61L 2202/24; A61L 2202/23; A61L 31/048; A61L 2202/181
See application file for complete search history.

(56) References Cited

U.S. PATENT DOCUMENTS

| | | | | |
|---|---|---|---|---|
| 5,167,632 | A | * | 12/1992 | Eid ..................... A61M 5/2033 604/136 |
| 8,293,173 | B2 | | 10/2012 | Bufano et al. |
| 2004/0182736 | A1 | | 9/2004 | Mesa et al. |
| 2005/0020979 | A1 | * | 1/2005 | Westbye ............. A61M 5/2033 604/151 |
| 2006/0054526 | A1 | * | 3/2006 | Dean ........................ A61L 2/28 206/459.1 |
| 2008/0183181 | A1 | * | 7/2008 | Treacy .................... A61L 2/206 606/108 |
| 2010/0280312 | A1 | | 11/2010 | D'Alessio et al. |
| 2011/0125100 | A1 | | 5/2011 | Schwirtz et al. |
| 2011/0288521 | A1 | * | 11/2011 | Bingham ................ A61M 5/30 604/500 |
| 2012/0114524 | A1 | | 5/2012 | Sigg |
| 2014/0027333 | A1 | * | 1/2014 | Pawlowski ........... A61M 5/001 206/438 |
| 2015/0073353 | A1 | | 3/2015 | Strader |
| 2015/0297765 | A1 | * | 10/2015 | Krueger ................. A61L 2/087 422/2 |

FOREIGN PATENT DOCUMENTS

| | | |
|---|---|---|
| CN | 204798475 | 11/2015 |
| CN | 105517583 | 4/2016 |
| CN | 105517602 | 4/2016 |
| EP | 1944044 | 7/2008 |
| WO | WO 94/07553 | 4/1994 |

OTHER PUBLICATIONS

App No. PCT/US2017/057525 International Search Report, dated May 18, 2018.
App No. PCT/US2017/057525 Written Opinion, dated May 18, 2018.
App No. PCT/US2017/057525 International Preliminary Report on Patentability, dated Apr. 23, 2019.
Hubbell et al., "Tables of X-Ray Mass Attenuation Coefficients and Mass Energy-Absorption," NIST, May 1995.
"Attenuation Coefficient," https://en.wikipedia.org/wiki/Attenuation_coefficient, Wikimedia Foundation, Inc., Retrieved on Nov. 4, 2021.
"Mass Attenuation Coefficient," https://en.wikipedia.org/wiki/Mass_attenuation_coefficient, Wikimedia Foundation, Inc., Retrieved on Nov. 4, 2021.
Pacansky et al., "Irradiation of Poly(Perfluoropropylene Oxide) by a 175 kV Electron Beam: The Formation and Hydrolosis of Acid Fluoride Groups," Journal of Fluorine Chemistry, Mar. 12, 1986.
"Technical Considerations for Pen, Jet, and Related Injectors Intended for Use with Drugs and Biological Products," FDA, 2009.
Grun, "Beta Dose Attenuation in Thin Layers," Ancient TL, 1986.
Communication Pursuant to Rule 164(2)(b) and Article 94(3) EPC in European Application No. 17791906.5, dated Sep. 24, 2021.

* cited by examiner

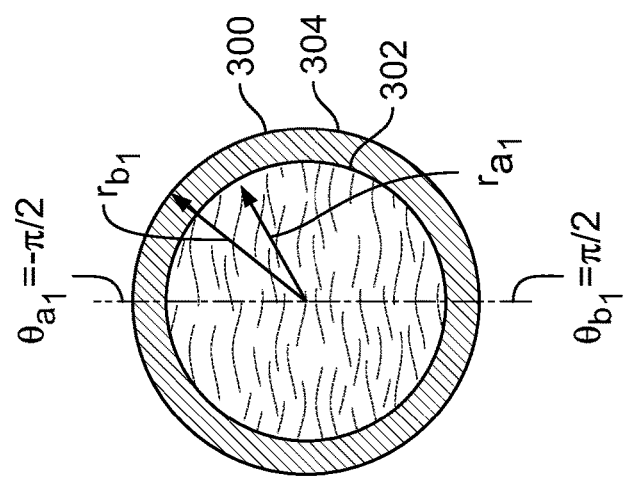
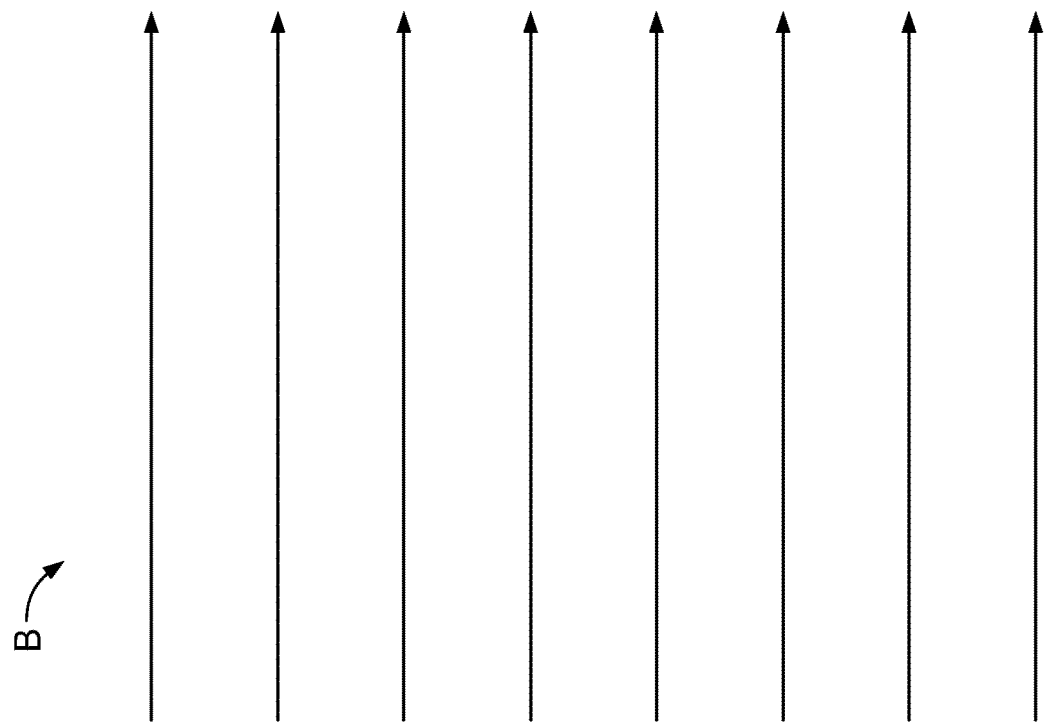
FIG. 3

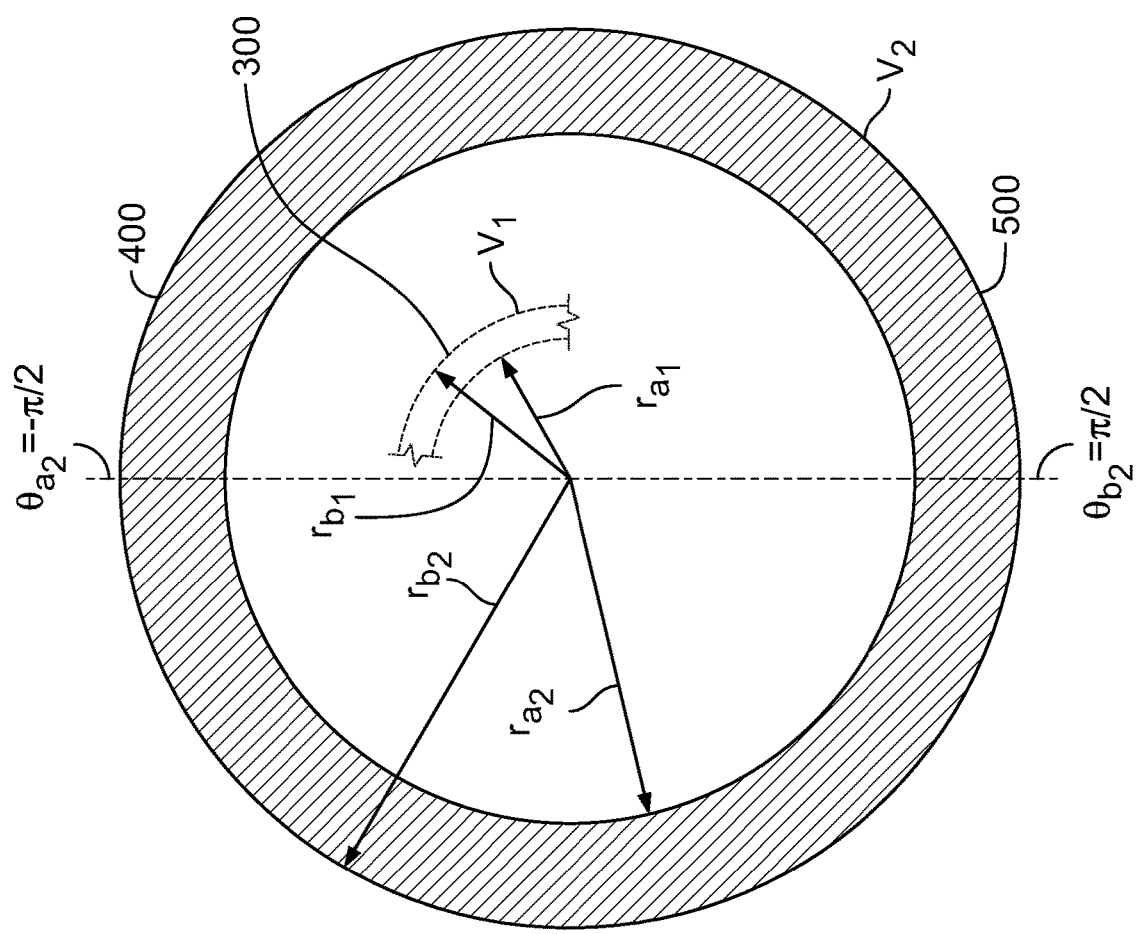
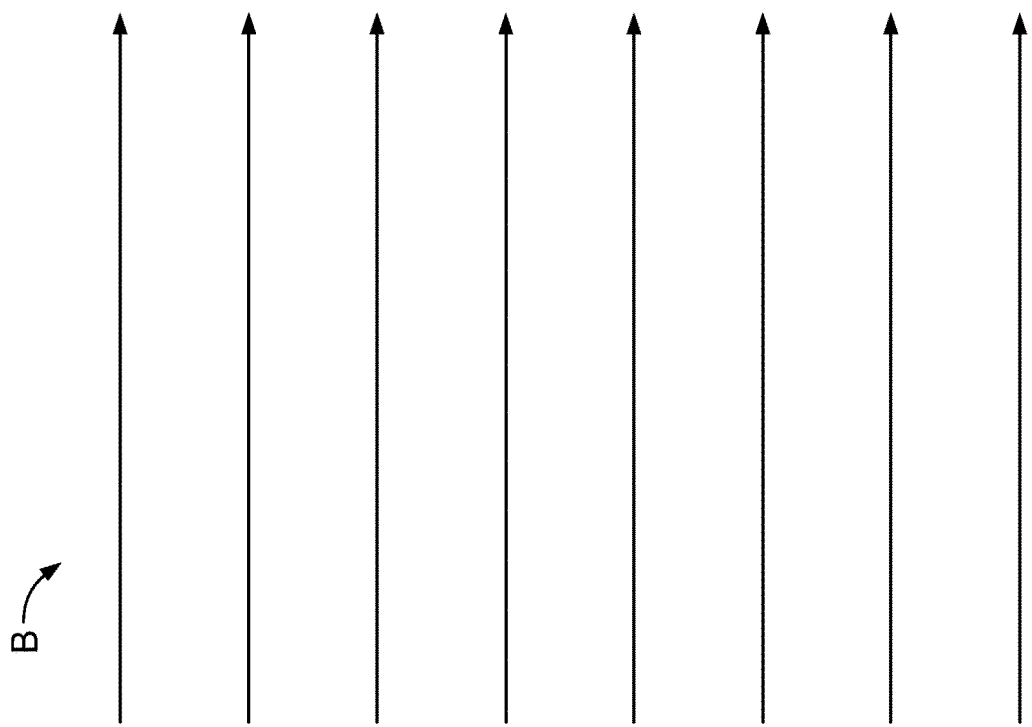
FIG. 5

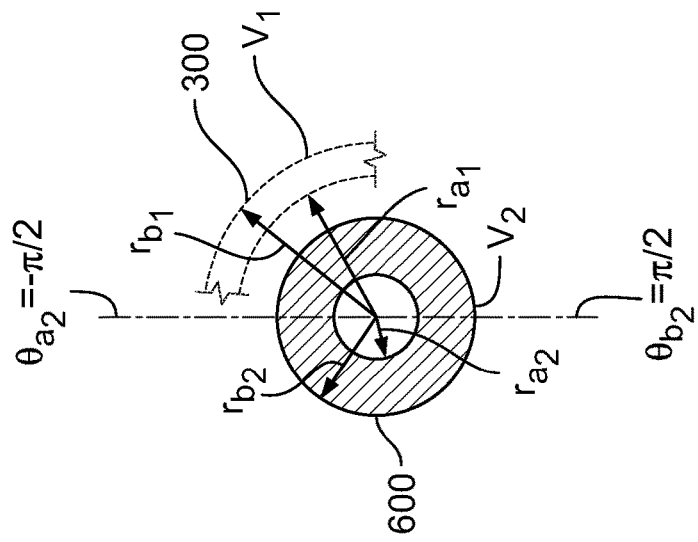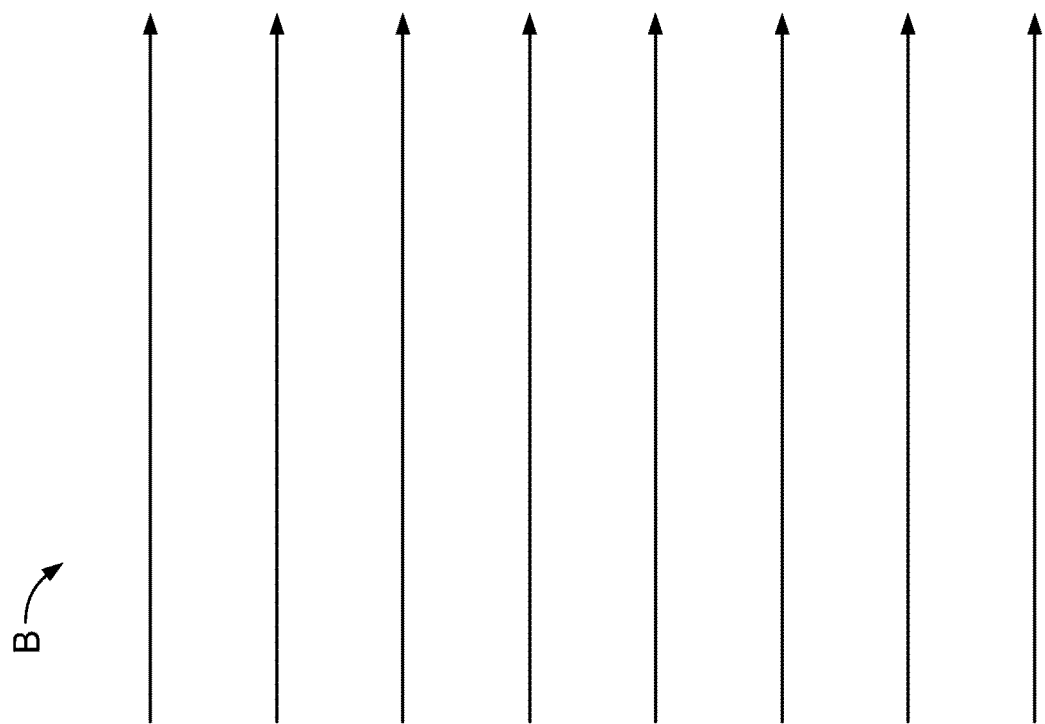
FIG. 6

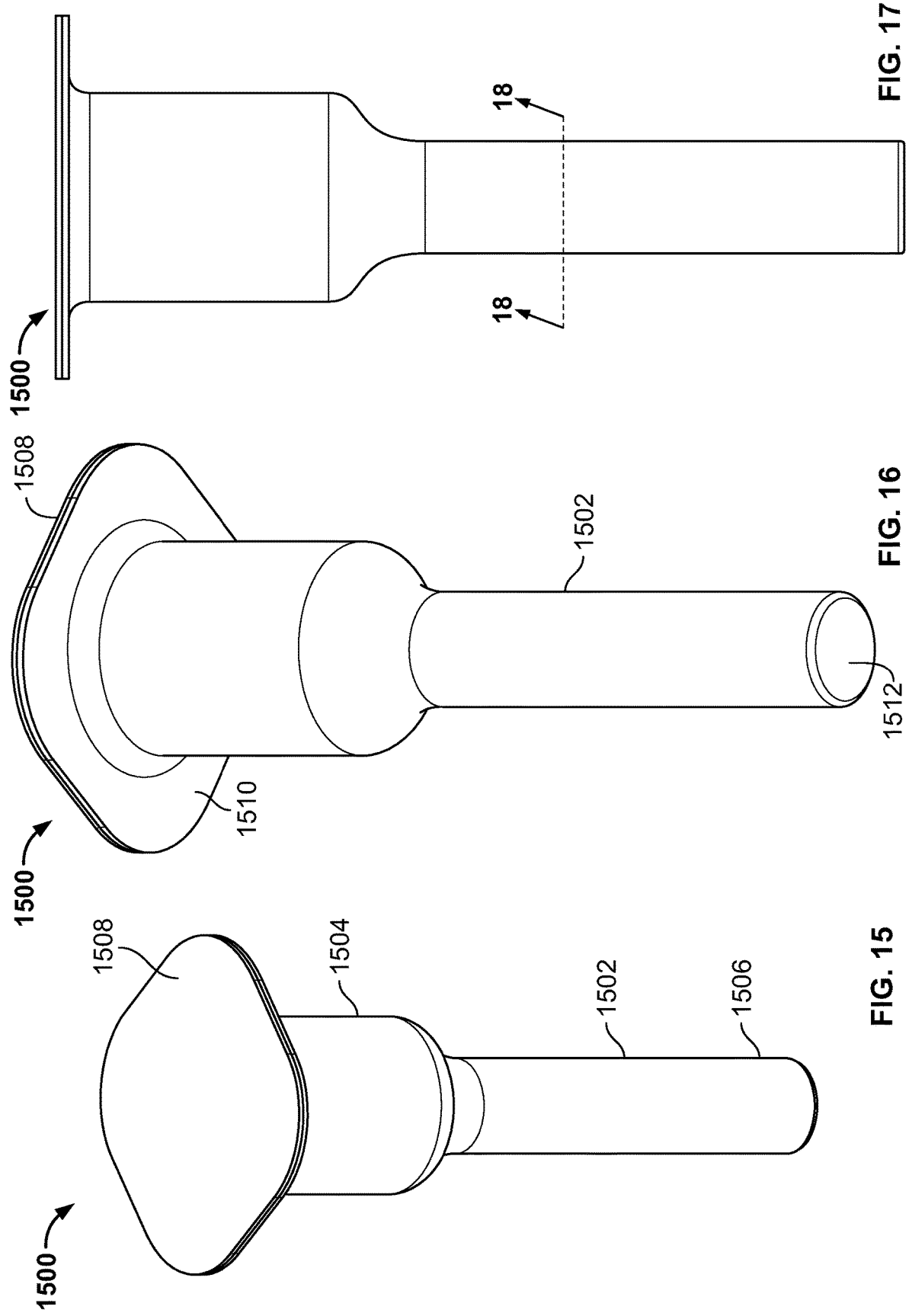

STERILE SEALED HETEROGENEOUS MEDICAMENT DELIVERY DEVICE

CROSS-REFERENCE TO RELATED APPLICATIONS

This application is a continuation of International Patent Application No. PCT/US2017/57525, filed on Oct. 20, 2017, which claims priority to U.S. Provisional Application No. 62/411,182, filed on Oct. 21, 2016, both of which are hereby incorporated by reference herein in their entireties.

BACKGROUND

Some medical devices are maintained in a sterile state preparatory to use. Such devices include medicament delivery devices. Manufacturers often ship medicament delivery devices in a sealed sterile envelope. Chemical sterilization processes may leave residue in the envelope. Radiation exposure sterilization may avoid residue. The exposure can occur with the device inside the envelope. The X-ray radiation can be provided by exposing the device to an X-ray source. The X-ray radiation can be provided by exposing the device to an electron beam, which is converted to Bremsstrahlung X-radiation at, or within a submillimeter region below, the surface of the device.

The radiation exposure can cause degradation of a medicament in the device. Different elements of the device can have different capacities to attenuate or absorb the radiation. Some elements can have internal surfaces that require sterilization. X-ray beams having different source energies or electron beam of different powers can be used to sterilize the different elements and surfaces.

Different elements requiring different source energies or electron beam powers can be sterilized separately. This typically requires a sterile field in which to attach the medicament delivery assembly to the medicament-housing elements.

It would be desirable therefore to provide apparatus that may be sterilized without the need for X-ray beams having different source energies.

It would be desirable therefore to provide apparatus that may be sterilized without the need for electron beams of different powers.

It also would be desirable therefore to provide apparatus that may be sterilized without requiring separate assembly of sterile parts after sterilization of the sterile parts.

BRIEF DESCRIPTION OF DRAWINGS

The objects and advantages of the invention will be apparent upon consideration of the following detailed description, taken in conjunction with the accompanying drawings, in which like reference characters refer to like parts throughout, and in which:

FIG. 3 shows a cross-sectional schematic representation of apparatus and processes in accordance with principles of the invention;

FIG. 5 shows a cross-sectional schematic representation of apparatus and processes in accordance with principles of the invention;

FIG. 6 shows a cross-sectional schematic representation of apparatus and processes in accordance with principles of the invention;

FIG. 15 shows a perspective view of illustrative apparatus in accordance with principles of the invention;

FIG. 16 shows another perspective view of apparatus shown in FIG. 15;

FIG. 17 shows another view of apparatus shown in FIG. 15;

DETAILED DESCRIPTION

Figure 1:
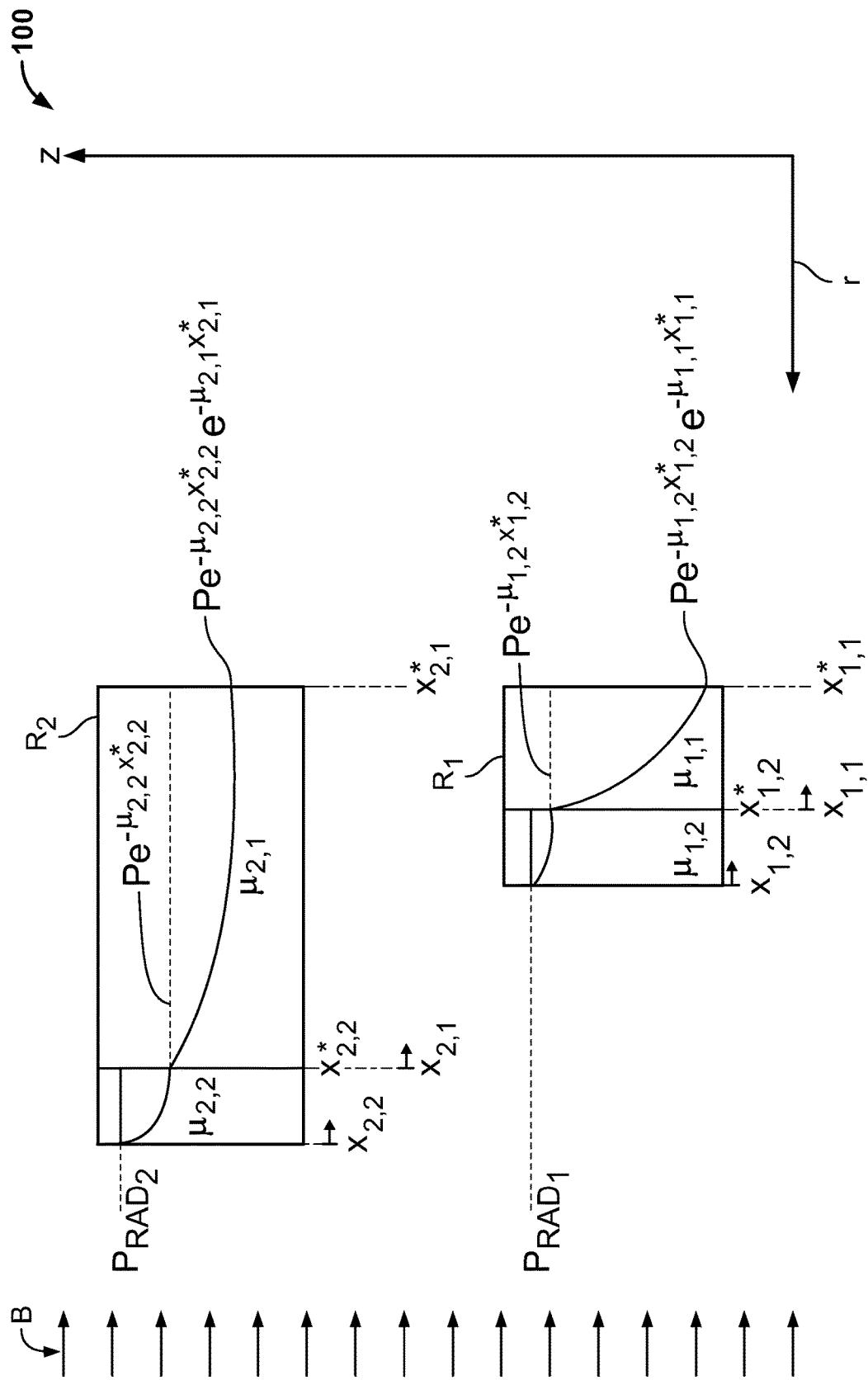
FIG. 1 illustrates a conceptual model in accordance with principles of the invention.

Apparatus and methods for delivering medicament to a patient are provided.

The apparatus may include elements, each of which has a distinct or different capacity to attenuate radiation or absorb radiation. For example, the apparatus may include a medicament delivery assembly with interactive elements for dose-setting, priming, medicament ejection, and the like. One or more elements of the medicament delivery assembly may house a radiation-sensitive medicament present in the apparatus during sterilization.

The capacity to attenuate radiation is referred to herein as "attenuation capacity." The capacity to absorb radiation is referred to herein as "absorption capacity." The term "radiative capacity" encompasses both "attenuation capacity" and "absorption capacity."

Quantification of radiation attenuation is discussed in X-Ray MASS ATTENUATION COEFFICIENTS by J. H. Hubbell and S. M. Seltzer, published online in May 1996 by NIST; MASS ATTENUATION COEFFICIENT by Wikipedia, published online on Apr. 7, 2016 by Wikimedia Foundation, Inc.; ATTENUATION COEFFICIENT by Wikipedia, published online on Jan. 16, 2016 by Wikimedia Foundation, Inc.; and IRRADIATION OF POLY(PERFLUOROPROPYLENE OXIDE) BY A 175 KV ELECTRON BEAM: THE FORMATION AND HYDROLYSIS OF ACID FLUORIDE GROUPS by J. Pacansky, R. J. Waltman and C. Wang, published by Elsevier in the Journal of Fluorine Chemistry on Mar. 12, 1986; each of which is incorporated herein in its entirety.

Table 1 shows illustrative mass attenuation coefficients for different materials that may be used in the apparatus. Values are given for the mean ratio of atomic number-to-mass Z/A, the mean excitation energy I, and the density. Some density values are only nominal.

TABLE 1

Illustrative Mass Attenuation Coefficients from Hubbel, 1996).

| Material | Z/A | I (eV) | Density (g/cm$^3$) | Composition (Z: fraction by weight) |
|---|---|---|---|---|
| Bakelite | 0.52792 | 72.4 | 1.250E+00 | 1: 0.057444 |
|  |  |  |  | 6: 0.774589 |
|  |  |  |  | 8: 0.167968 |
| Glass, Borosilicate (Pyrex) | 0.49707 | 134.0 | 2.230E+00 | 5: 0.040066 |
|  |  |  |  | 8: 0.539559 |
|  |  |  |  | 11: 0.028191 |
|  |  |  |  | 13: 0.011644 |
|  |  |  |  | 14: 0.377220 |
|  |  |  |  | 19: 0.003321 |
| Polyethylene | 0.57033 | 57.4 | 9.300E−01 | 1: 0.143716 |
|  |  |  |  | 6: 0.856284 |
| Polyethylene, Terephthalate (Mylar) | 0.52037 | 78.7 | 1.380E+00 | 1: 0.041960 |
|  |  |  |  | 6: 0.625016 |
|  |  |  |  | 8: 0.333024 |
| Polymethyl Methacrylate | 0.53937 | 74.0 | 1.190E+00 | 1: 0.080541 |
|  |  |  |  | 6: 0.599846 |
|  |  |  |  | 8: 0.319613 |
| Polystyrene | 0.53768 | 68.7 | 1.060E+00 | 1: 0.077421 |
|  |  |  |  | 6: 0.922579 |
| Polytetrafluoroethylene (Teflon) | 0.47993 | 99.1 | 2.250E+00 | 6: 0.240183 |
|  |  |  |  | 9: 0.759818 |
| Polyvinyl Chloride | 0.51201 | 108.2 | 1.406E+00 | 1: 0.048382 |
|  |  |  |  | 6: 0.384361 |
|  |  |  |  | 17: 0.567257 |

The apparatus may include a chamber. The chamber may contain the medicament. The chamber may have a medicament delivery outlet.

The apparatus may include a delivery assembly. The delivery assembly may include an actuator chassis. The delivery assembly may include a drive mechanism. The delivery assembly may include a needle-priming mechanism. The delivery assembly may include a fluid-displacement mechanism. The fluid-displacement mechanism may include one or more hollow regions. A hollow region may reduce beam attenuation. A hollow region may reduce radiation absorption. The delivery assembly may have any other suitable elements. Delivery assembly elements may be nested. Delivery assembly elements may be nested coaxially. Delivery assembly elements may be stacked. Delivery assembly elements may be stacked axially.

The chassis may be fixed to the chamber. The chassis may be fixed, relative to the outlet, to the chamber. The fluid-displacement member may be engaged with the chassis. The fluid-displacement member may be slidingly engaged with the chassis. The fluid-displacement member may be threadingly engaged with the chassis. The fluid-displacement member may be configured to move relative to the outlet to move the medicament through the outlet.

The chamber may be collapsible. The fluid-displacement member may collapse the chamber to deliver the medicament.

The apparatus may include an envelope. The envelope may sterilely surround the chassis. The envelope may be an envelope that encloses no residue from chemical sterilization. The sterilization may be adequate for use in a sterile field. The sterilization may be adequate for ophthalmic use. The sterilization may be adequate for use in an operating room.

"Sterile" may satisfy one or more known standards. For example, "sterile" may be defined as in ANSI/AAMI ST67, which is hereby incorporated herein in its entirety. ("Generally an SAL [Sterility Assurance Level] value of $10^{-6}$ has been used for terminal sterilization of health care products." "A terminally sterilized product with an SAL of greater than $10^{-3}$, e.g., $10^{-2}$, $10^{-2}$, etc., shall not be labeled as sterile.")

"Sterile" for the apparatus may correspond to "sterile" for an injector. Data for a sterile injector may demonstrate a probability of a non-sterile unit not greater than $1 \times 10^{-6}$. See, for example, FDA, "Technical Considerations for Pen, Jet, and Related Injectors Intended for Use with Drugs and Biological Products" guidance document, which is hereby incorporated herein in its entirety.

The chassis may be fixed to the chamber, and support the fluid-displacement member, so that the fluid-displacement member, when moved relative to the chassis, moves relative to the chamber, and pushes the medicament out through the outlet. The chassis may support any suitable drive mechanism for driving the fluid-displacement mechanism in linear motion. The chassis may support any suitable drive mechanism for driving the fluid-displacement mechanism in rotational motion. The chassis may support any suitable drive mechanism for driving the fluid-displacement mechanism in helical motion. The mechanism may include a knob or button that an operator may push. The mechanism may include a finger flange.

The chassis may support any suitable needle-priming mechanism. The chassis may support any suitable dose-setting mechanism.

The drive mechanism may be disposed in part or in whole within the chassis. The priming mechanism may be disposed in part or in whole within the chassis. The dose-setting mechanism may be disposed in part or in whole within the chassis.

The chassis may be fixed to the chamber by virtue of the chassis's fixation to a barrel of which the chamber is part. The chassis may be disposed coaxially with the barrel. The chassis may abut the barrel. The chassis may be fixed by adhesive to the barrel.

The chamber may be in whole or in part lodged within the chassis. The barrel may be in whole or in part lodged within the chassis. The chassis may enclose, in whole or in part, one or more of the drive mechanism, the priming mechanism, the displacement member, the chamber and the barrel.

The chassis may be in whole or in part lodged within the chamber. The chassis may be in whole or in part lodged within the barrel. One or more of the drive mechanism, the priming mechanism, the displacement member, the chamber and the barrel may enclose, in whole or in part, the chassis.

The fluid-displacement member may include a shaft. The fluid-displacement member may include a plunger. The fluid-displacement member may include a flange. The flange may be configured to receive part of an operator's thumb or finger. The fluid-displacement member may include a hinge. The hinge may be a living hinge. The fluid-displacement member may include a flap. The fluid-displacement member may include an elastic energy storage device. The elastic energy storage device may include a spring. The fluid-displacement member may include a permanent magnet. The fluid-displacement member may include a ferrous member. The ferrous member may be configured to perform as an electromagnet.

The fluid-displacement member may include a membrane. The membrane may include a diaphragm. The membrane may be stretchable. The membrane may be expandable.

Models for quantifying the relative attenuation of different elements of the apparatus are discussed below.

One-Dimensional Linear Mass Attenuation Model

FIG. 1 shows illustrative conceptual model 100 of "attenuation capacity" in two regions, $R_1$ and $R_2$, of an apparatus. $R_1$ and $R_2$ are at different locations along axis z of the apparatus, and extend away from axis z along the r axis. $R_1$ may represent a portion of a medicament delivery assembly having one element with mass attenuation coefficient $\mu_{1,1}$ and a second having mass attenuation coefficient $\mu_{1,2}$. $R_2$ may represent a chamber wall having mass attenuation coefficient $\mu_{2,1}$ and a sheath having mass attenuation coefficient $\mu_{2,2}$. One or both of $R_1$ and $R_2$ may have a number of elements that is different from the number shown.

The "attenuation capacities" ($C_A$) of $R_1$ and $R_2$ may be defined, respectively, as:

$$C_{A_1} = P_{RAD_1} e^{-\mu_{1,2} x^*_{1,2}} e^{-\mu_{1,1} x^*_{1,1}}, \quad \text{Eq'n. 1,}$$

$$C_{A_2} = P_{RAD_2} e^{-\mu_{2,2} x^*_{2,2}} e^{-\mu_{2,1} x^*_{2,1}}, \quad \text{Eq'n. 2}$$

wherein:

$P_{RAD_1}$ and $P_{RAD_2}$ are the powers of the X-ray beam just inside the surface of $R_1$ and $R_2$, respectively;

$\mu_{1,i}$ is the mass attenuation coefficient for the ith element of $R_1$;

Energy beam B may be directed at $R_1$ and $R_2$ along the z axis.

$\mu_{2,j}$ is the mass attenuation coefficient for the jth element of $R_2$;

$x^*_{1,i}$ is the thickness of the ith element of $R_1$; and $x^*_{2,j}$ is the thickness of the jth element of $R_2$; and Energy beam B is shown directed at $R_1$ and $R_2$ toward the z axis.

The one-dimensional relative attenuation capacity of $R_1$ and $R_2$ may be expressed as quotient $Q_{1D}$, as set forth in illustrative Equations 3-4.

$$Q_{1D} = \frac{C_{A_1}}{C_{A_2}}, \quad \text{Eq'n. 3}$$

$$= \frac{P_{RAD_1}}{P_{RAD_2}} e^{(\mu_{2,2} x^*_{2,2} + \mu_{2,1} x^*_{2,1}) - (\mu_{1,2} x^*_{1,2} + \mu_{1,1} x^*_{1,1})}, \quad \text{Eq'n. 4}$$

Q provides a comparison between the capacities of the two elements, and may characterize the relative shielding effect of the elements when the flux of energy in electron beam B has the same intensity and shape when irradiating the two elements.

When a first attenuation capacity is greater than a second attenuation capacity, the first attenuation capacity may be expressed as being a multiple of the second attenuation capacity. The multiple may be the quotient.

When B is an X-ray beam, $P_{RAD_1}$ and $P_{RAD_2}$ will be the same, so $$Q_{X\text{-}ray} = e^{(\mu_{2,2} x^*_{2,2} + \mu_{2,1} x^*_{2,1}) - (\mu_{1,2} x^*_{1,2} + \mu_{1,1} x^*_{1,1})}, \quad \text{Eq'n. 5.}$$

For I elements i of $R_1$ and J elements j of $R_2$, $$Q_{X\text{-}ray} = e^{\Sigma_{j=1}^{J} \mu_{2,j} x^*_{2,j} - \Sigma_{i=1}^{I} \mu_{1,i} x^*_{1,i}}, \quad \text{Eq'n. 6.}$$

If B is an electron beam having power $P_{EB}$, $$P_{RAD_1} = P_{EB} k Z_1 V_{EB}, \quad \text{Eq'n. 7., and}$$

$$P_{RAD_2} = P_{EB} k Z_2 V_{EB}, \quad \text{Eq'n. 8.,}$$

wherein $Z_1$ and $Z_2$ are the atomic numbers of the material in $R_1$ and $R_2$, respectively and $V_{EB}$ is the voltage of B. Therefore, for Equation 4, $$\frac{P_{RAD_1}}{P_{RAD_2}} = \frac{Z_1}{Z_2} P_{EB} k V_{EB}, \quad \text{Eq'n. 9}$$

Equation 9 assumes that $V_{EB}$ is the same for $R_1$ and $R_2$. When different beams are used for the different regions, each region may be exposed to different beam voltages, V. For example, the radiation may be attenuated inside the apparatus by one or more apparatus components, which may have different material properties, and may be disposed longitudinally with respect to each other, and may attenuate the radiation at different rates.

When the material is a complex molecule or a polymer, $Z_1$ and $Z_2$ may be determined by an empirical relationship. The empirical relationship may depend on bulk density of the material. Examples of such relationships are set forth in R. Grun "Beta dose attenuation in thin layers," Ancient TL, 1986, which is hereby incorporated by reference herein in its entirety.

Table 2 shows illustrative potential and power of energy beam B, as an electron beam.

TABLE 2

Illustrative Electron Beam Potential and Power.

| Electron Beam Potential, limits inclusive, keV (lower limit only, where no upper limit is given) | | | Electron Beam Power, limits inclusive, keV (lower limit only, where no upper limit is given) | | |
|---|---|---|---|---|---|
| Illustrative Approximate Beam strength | Lower | Upper | Illustrative Approximate Beam Power | Lower | Upper |
| 10 | 10 | 20 | 4.03E−03 | 4.03E−03 | 1.61E−02 |
| 20 | 20 | 40 | 1.61E−02 | 1.61E−02 | 4.76E−02 |
| 40 | 40 | 80 | 4.76E−02 | 4.76E−02 | 1.54E−01 |
| 80 | 80 | 130 | 1.54E−01 | 1.54E−01 | 3.42E−01 |
| 130 | 130 | 200 | 3.42E−01 | 3.42E−01 | 6.85E−01 |
| 200 | 200 | 250 | 6.85E−01 | 6.85E−01 | 9.77E−01 |
| 250 | 250 | — | 9.77E−01 | 9.77E−01 | — |

When the energy beam is an X-ray beam, the source generates X-rays that in the aggregate have a distribution of energies, based on the source energy. Most of the energies are below the potential of the beam. Table 3 shows illustrative X-ray source energies.

TABLE 3

Illustrative X-ray Beam Source Energies.

| Illustrative Approximate Source Energy, KeV | Illustrative Ranges of Source Energy, KeV, inclusive of endpoints |
|---|---|
| <9 | 9-11 |
| 9 | 11-12 |
| 10 | 12-13 |
| 11 | 13-14 |
| 12 | 14-15 |
| 13 | 15-16 |
| 14 | 16-17 |
| 15 | 17-18 |
| 16 | 18-19 |
| 17 | 19-20 |
| 18 | 21-22 |
| 19 | 22-23 |
| 20 | 23-24 |
| 21 | 24-25 |
| 22 | 25-26 |
| 23 | 9-11 |
| 24 | 11-13 |
| >25 | 13-15 |
|  | 15-17 |
|  | 17-19 |
|  | 19-21 |
|  | 21-23 |
|  | 23-25 |
|  | 8-12 |
|  | 12-16 |
|  | 16-20 |
|  | 20-24 |

Volume-Based Mass Absorption Model

Figure 2:
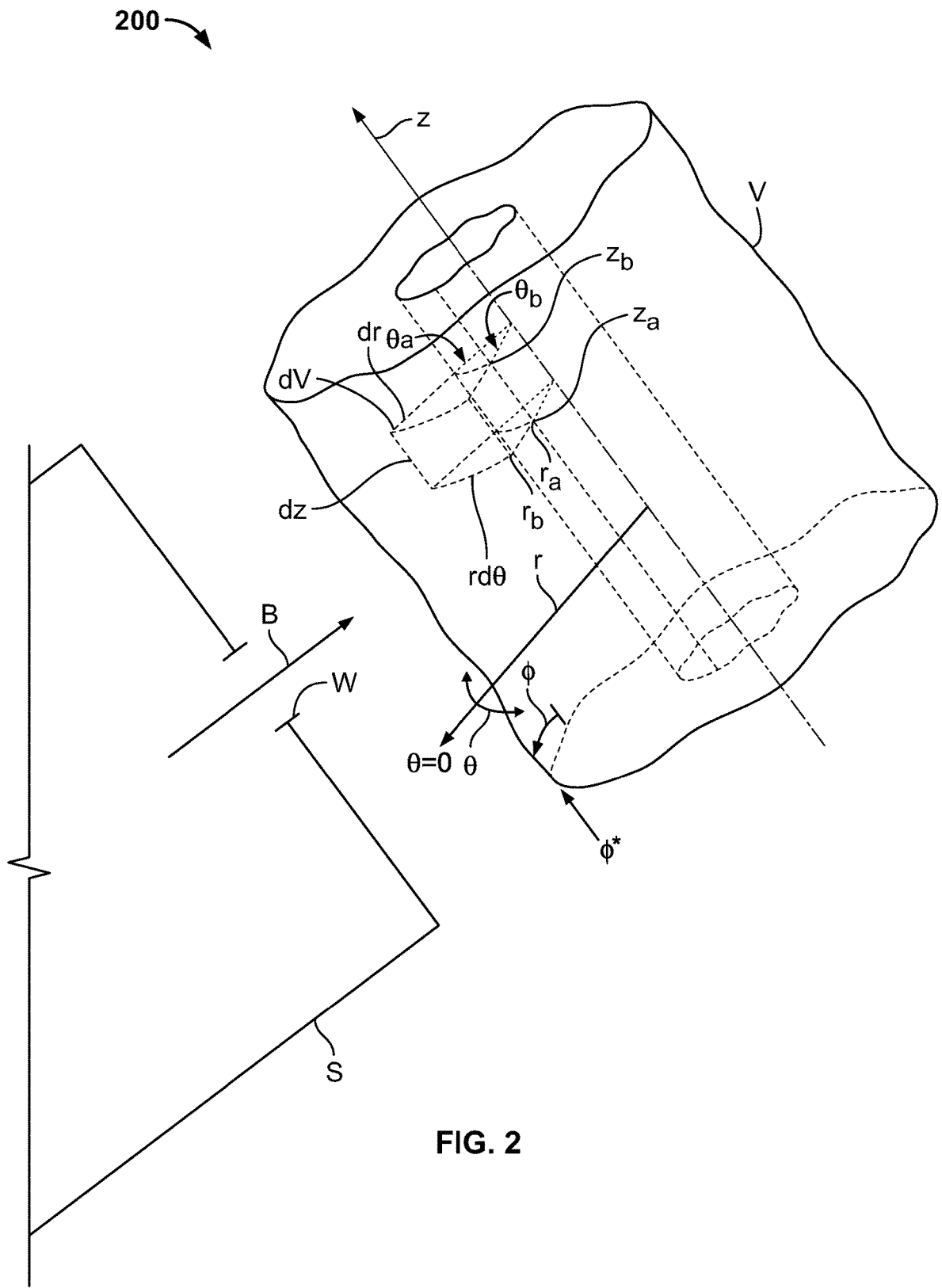
FIG. 2 illustrates the conceptual model of FIG. 1 applied to a volume.

FIG. 2 shows illustrative conceptual model 200 of absorption capacity in a volume, such as volume V, which may represent, in whole or in part, an apparatus element, such as the delivery assembly, the chamber, the envelope, the sheath or any other suitable element. Model 200 may represent an application of model 100 (shown in FIG. 1) to the volume.

$\phi^*$ represents the angular position of V, about the z-axis, relative to energy beam B. Energy beam B is shown as being collimated. Energy beam B may have any suitable cross-sectional profile. Energy beam B may include an X-ray beam. The X-ray beam may include Bremsstrahlung radiation.

V may be toroidal. V may be annular. V may be cylindrical. V may be rectilinear. V may be irregular. V may include one or more elements or element constituents. V may include void spaces between the elements or constituents. V may have spatially non-uniform mass distribution. V may have spatially non-uniform atomic number distribution. V may have spatially non-uniform mass density. V may have spatially non-uniform atomic number density.

V may absorb or scatter energy of electron beam B, which is emitted by source S through window W. The absorption capacity of an element may depend on mass density. The absorption capacity of an element may depend on atomic number density. The absorption capacity of an element may depend on the spatial distribution of mass V.

dV is a differential volume of V. Equation 10 gives an illustrative expression of the differential absorption capacity dC of dV.

$$dC = \rho(r, \theta, z)dV, \quad \text{Eq'n. 10,}$$

in which $\rho$ is the volumetric density of atomic number, or any other suitable unit that attenuates a beam such as B, and cylindrical coordinates r, $\theta$ and z are as shown.

Illustrative equations 11-13 illustrate one way in which absorption capacity can be generalized to V of arbitrary geometry.

$$C = \int dC, \quad \text{Eq'n. 11}$$

$$= \int \rho(r, \theta, z)dV, \quad \text{Eq'n. 12}$$

$$= \int_{r=r_a}^{r_b} \int_{\theta=\theta_a}^{\theta_b} \int_{z=z_a}^{z_b} r\rho(r, \theta, z)dr \cdot d\theta \cdot dz, \quad \text{Eq'n. 13}$$

C for any geometry may be expressed, by analogy, in rectilinear, spherical or any other suitable coordinate system.

$r_a$ greater than zero may express a hollow element. $r_a$ greater than zero may define an interior surface of an element. A different element may be disposed inside the interior surface. $r_a$ equal to zero may express an element having a solid core.

$\rho$ may vary within V with one or more of r, $\theta$ and z. If there is more than one element V that contributes to absorption capacity, for an assembly of parts, for example, the total capacity may be constructed as set forth in illustrative Equations 14-15:

$$C_{total} = \Sigma_{i=1}^{I} \int dC_i, \quad \text{Eq'n. 14,}$$

wherein:

$$\int dC_i = \int_{r=r_{a_i}}^{r_{b_i}} \int_{\theta=\theta_{a_i}}^{\theta_{b_i}} \int_{z=z_{a_i}}^{z_{b_i}} r\rho_i(r, \theta, z)dr \cdot d\theta \cdot dz, \quad \text{Eq'n. 15}$$

wherein each of the i elements has ith limits in r, z and $\theta$, and an ith $\rho$.

Coaxially nested volumes, each having a distinct absorption capacity, may be expressed using Equation 5 with Equation 16, in which the limits of z and $\theta$ do not change with i:

$$\int dC_i = \int_{r=r_{a_i}}^{r_{b_i}} \int_{\theta=\theta_a}^{\theta_b} \int_{z=z_a}^{z_b} r\rho_i(r, \theta, z)dr \cdot d\theta \cdot dz, \quad \text{Eq'n. 16}$$

$C_{total}$ for elements may be calculated, whether in cylindrical, rectilinear, spherical, or other coordinate systems.

The absorptive capacities of one or more elements may be compared to each other by calculating a ratio. The ratio may be expressed as a multiple. The ratio may be expressed as a quotient. For example, the absorptive capacity of a first element (for example, the chamber, having a volume $V_1$) may be compared to the absorptive capacity of a second element (for example, the delivery assembly, having a volume $V_2$).

The relative absorption capacity of two element volumes $V_1$ and $V_2$ may be expressed as quotient $Q_{3D}$, such as in illustrative Equations 17-18.

$$Q_{3D} = \frac{C_1}{C_2}, \quad \text{Eq'n. 17}$$

-continued $$= \frac{\int_{r=r_{a_1}}^{r_{b_1}} \int_{\theta=\theta_{a_1}}^{\theta_{b_1}} \int_{z=z_{a_1}}^{z_{b_1}} r\rho_1(r, \theta, z) dr \cdot d\theta \cdot dz}{\int_{r=r_{a_2}}^{r_{b_2}} \int_{\theta=\theta_{a_2}}^{\theta_{b_2}} \int_{z=z_{a_2}}^{z_{b_2}} r\rho_2(r, \theta, z) dr \cdot d\theta \cdot dz},$$ Eq'n. 18

Ratio $Q_{3D}$ provides a comparison between the capacities of the two elements, and may predict the shielding effect of the elements when the flux of energy in electron beam B has the same intensity and shape when irradiating the two elements, and when $\phi^*$ (shown in FIG. 2) is the same when irradiating the two elements.

Limits of the integrals in $Q_{3D}$ may be set differently from those expressed in Equation 9. The limits may capture features of the shapes of $V_1$ and $V_2$. Table 4 lists illustrative examples of limits, one or more of which may be employed in a formulation of $Q_{3D}$.

TABLE 4

Illustrative other formulations of $Q_{3D}$.

| Features to capture | Illustrative limits for Equation 18 |
| --- | --- |
| Evaluate $Q_{3D}$ for longitudinal section of $V_1$ and corresponding longitudinal section of $V_2$ | $z_{b_1} - z_{a_1} = z_{b_2} - z_{a_2}$. |
| Focus $Q_{3D}$ on angular sector where $V_1$ has exposure to e-beam for a given position $\phi$. | $\theta_{a_1} = \theta_{EB_1}$; $\theta_{b_1} = -\theta_{EB_1}$; $\theta_{a_2} = \theta_{EB_2}$; $\theta_{b_2} = -\theta_{EB_2}$; where $\theta_{EB_i}$ corresponds to the angle required to encompass half of the electron beam width impinging on $V_i$. |
| Focus Q on angular sector where $V_2$ has a maximum radius. | $\theta_{a_2} = \theta_{rmax_2}$; $\theta_{b_2} = -\theta_{rmax_2}$; $\theta_{a_1} = \theta_{a_2}$; $\theta_{b_1} = \theta_{b_2}$, where $\theta_{rmax_2}$ and $-\theta_{rmax_2}$ bound all, some, or a significant portion (say, 97% by mass, volume or atomic number) of the excess of the maximum radius over, say, a mean radius for all $\theta_2$. |

FIG. 3 shows conceptually a schematic cross-section of illustrative element 300. Element 300 may contain medicament 302. Electron beam B, shown incident on chamber 300, may be used to sterilize outer surface 304 of chamber 300.

Figure 4:
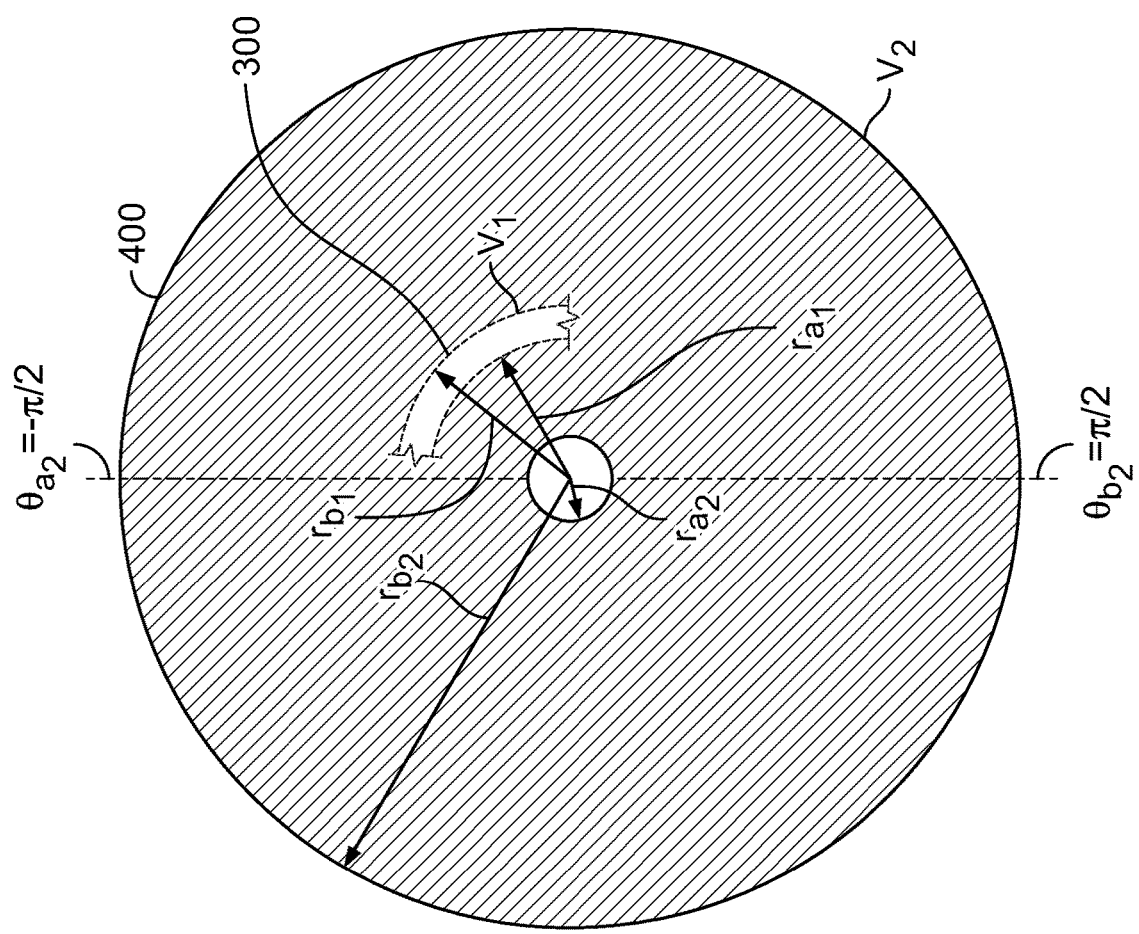
FIG. 4 shows a cross-sectional schematic representation of apparatus and processes in accordance with principles of the invention.

FIG. 4 shows conceptually a schematic cross-section of illustrative element 400. Element 400 may be, in part or in whole, offset along axis z from element 300 (shown in FIG. 3). Element 400 may have inner radius $r_{a_2}$ that may be smaller than inner radius $r_{a_1}$ of element 300. Element 400 may have outer radius $r_{b_2}$ that may be greater than outer radius $r_{b_1}$ of element 300. A segment of element 300 is shown for reference.

FIG. 5 shows conceptually a schematic cross-section of illustrative element 500. Element 500 may be, in part or in whole, offset along axis z from element 300 (shown in FIG. 3). Element 500 may have inner radius $r_{a_2}$ that may be greater than outer radius $r_{b_1}$ of element 300. Element 500 may have outer radius $r_{b_2}$ that may be greater than outer radius $r_{b_1}$ of element 300. A segment of element 300 is shown for reference.

FIG. 6 shows conceptually a schematic cross-section of illustrative delivery assembly element 600. Element 600 may be, in part or in whole, offset along axis z from element 300 (shown in FIG. 3). Element 600 may have inner radius $r_{a_2}$ that may be lesser than inner radius $r_{a_1}$ of element 300. Element 600 may have outer radius $r_{b_2}$ that may be lesser than inner radius $r_{a_1}$ of element 300. A segment of element 300 is shown for reference.

Figure 7:
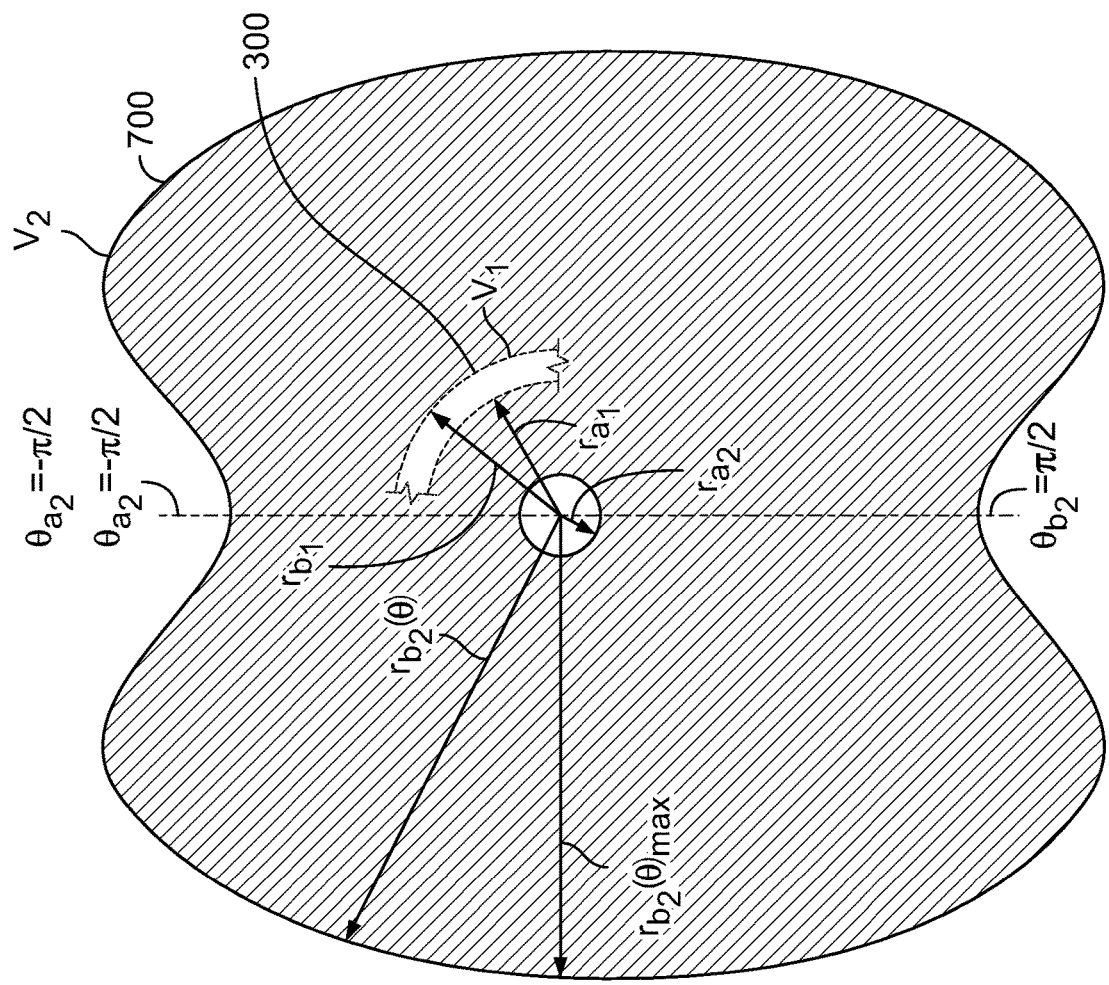
FIG. 7 shows a cross-sectional schematic representation of apparatus and processes in accordance with principles of the invention.

FIG. 7 shows conceptually a schematic cross-section of illustrative delivery assembly element 700. Element 700 may be, in part or in whole, offset along axis z from element 300 (shown in FIG. 3). Element 700 may have inner radius $r_{a_2}$ that may be smaller than inner radius $r_{a_1}$ of element 300. Element 700 may have outer radius $r_{b_2}$ that may be greater than outer radius $r_{b_1}$ of element 300. A segment of element 300 is shown for reference. $r_{b_2}$ may vary with $\theta$ (as $r_{b_2}(\theta)$).

$r_{b_2}$ may have one or more maximum values $r_{b_2}(\theta)_{max}$. $r_{b_2}(\theta)_{max}$ may be greater than $r_{b_1}$. $r_{b_2}(\theta)_{max}$ may be lesser than $r_{b_1}$. $r_{b_2}(\theta)_{max}$ may be greater than $r_{a_1}$. $r_{b_2}(\theta)_{max}$ may be lesser than $r_{a_1}$.

$r_{b_2}$ may have one or more minimum values $r_{b_2}(\theta)_{min}$. $r_{b_2}(\theta)_{min}$ may be greater than $r_{b_1}$. $r_{b_2}(\theta)_{min}$ may be lesser than $r_{b_1}$. $r_{b_2}(\theta)_{min}$ may be greater than $r_{a_1}$. $r_{b_2}(\theta)_{min}$ may be lesser than $r_{a_1}$.

By analogy with $r_{b_2}(\theta)$, one or more of $r_{a_2}$, $r_{b_1}$ and $r_{a_1}$ may vary with $\theta$. By analogy with $r_{b_2}(\theta)$, one or more of $r_{a_2}$, $r_{b_1}$ and $r_{a_1}$ may have one or more maximum. By analogy with $r_{b_2}(\theta)$, one or more of $r_{a_2}$, $r_{b_1}$ and $r_{a_1}$ may have one or more minimum.

$r_{b_2}$ may have one or more maximum values $r_{b_2}(z)_{max}$. $r_{b_2}(z)_{max}$ may be greater than $r_{b_1}(z)$. $r_{b_2}(z)_{max}$ may be lesser than $r_{b_1}(z)$. $r_{b_2}(z)_{max}$ may be greater than $r_{a_1}(z)$. $r_{b_2}(z)_{max}$ may be lesser than $r_{a_1}(z)$.

$r_{b_2}$ may have one or more minimum values $r_{b_2}(z)_{min}$. $r_{b_2}(z)_{min}$ may be greater than $r_{b_1}(z)$. $r_{b_2}(z)_{min}$ may be lesser than $r_{b_1}(z)$. $r_{b_2}(z)_{min}$ may be greater than $r_{a_1}(z)$. $r_{b_2}(z)_{min}$ may be lesser than $r_{a_1}(z)$.

By analogy with $r_{b_2}(z)$, one or more of $r_{a_2}$, $r_{b_1}$ and $r_{a_1}$ may vary with z. By analogy with $r_{b_2}(z)$, one or more of $r_{a_2}$, $r_{b_1}$ and $r_{a_1}$ may have one or more maximum. By analogy with $r_{b_2}(z)$, one or more of $r_{a_1}$, $r_{b_1}$ and $r_{a_1}$ may have one or more minimum.

Figure 8:
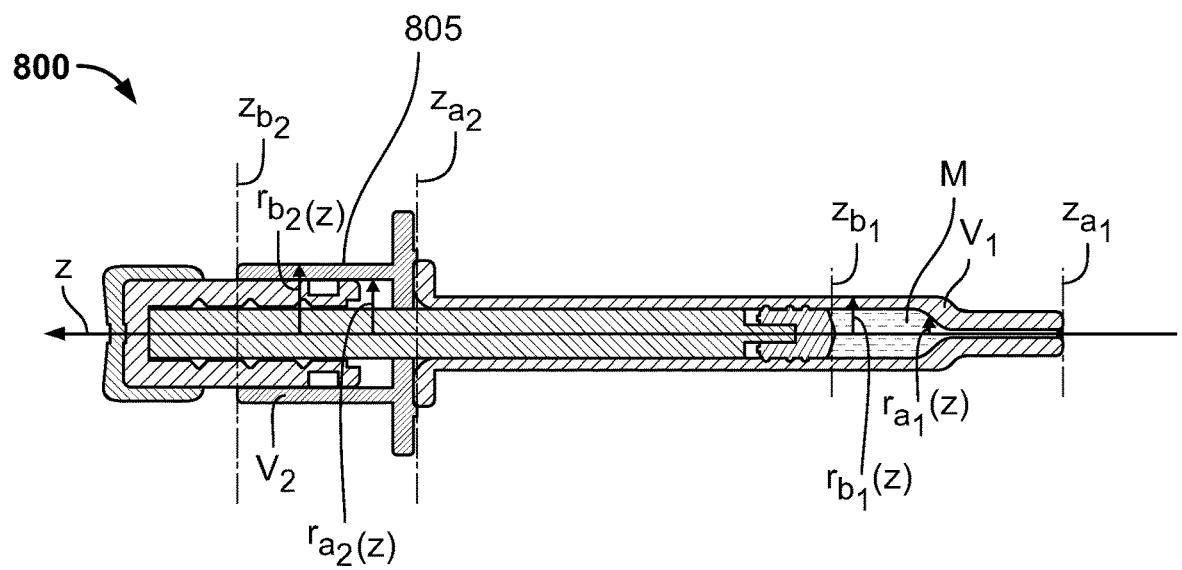
FIG. 8 shows in cross-sectional view illustrative apparatus in accordance with principles of the invention.

FIG. 8 shows conceptually variations of element radii with z in apparatus 800. Apparatus 800 may include collar 805. $V_1$ and $V_2$ may be elements that correspond to the conceptual $V_1$s and $V_2$s shown in FIGS. 3-7. They are spaced apart along z, distributed along z and r, and extend circumferentially out of the page in θ. M represents a medicament.

Figure 9:
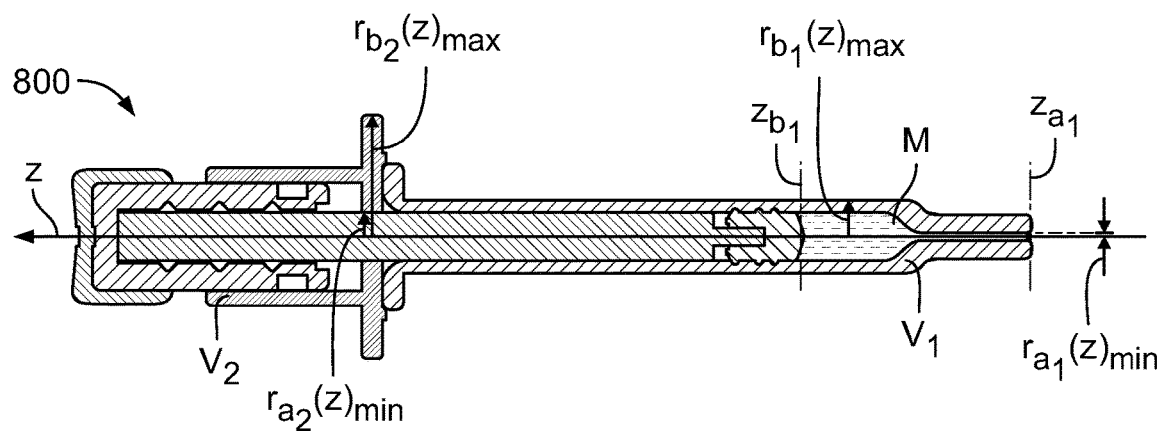
FIG. 9 shows the apparatus of FIG. 8.

FIG. 9 shows for apparatus 800 illustrative extreme values $r_{a_1}(z)_{min}$, $r_{b_1}(z)_{max}$, $r_{b_2}(z)_{max}$ and $r_{a_2}(z)_{min}$.

The chamber may be part of a prefilled syringe. The prefilled syringe may have a barrel that includes glass, plastic or any other suitable material. The prefilled syringe may include an integral needle. The prefilled syringe may be a prefilled syringe that does not include an integral needle. The prefilled syringe may include a needle safety shield.

The chamber may be part of prefilled syringe for an autoinjector. The chamber may be part of a cartridge for an autoinjector. The autoinjector may be used in an operating room environment. The autoinjector may be used in the vicinity of immunocompromised patients.

The chamber may be part of a patch pump. The patch pump may be a wearable infusion pump. The pump may deliver an injection up to tens of milliliters over a period of minutes. The pump may deliver an injection up to tens of milliliters over a period of days.

The chamber may be part of a drug vial. The vial may include plastic, glass, or any other suitable material. The vial may include a polymeric stopper.

The chamber may be part of a glass drug ampule.

The chamber may be part of a single-use dropper bottle.

The chamber may be part of a multi-use dropper bottle. The bottle may include plastic. The bottle may include a backflow prevention mechanism to prevent flow back into the dropper bottle.

The chamber may have a first radiation capacity. The delivery assembly may have a second radiation capacity. The first and second electron beam absorption capacities may be different. The difference may be a difference between the first and second electron beam absorption capacities on a per-unit-length-of-device basis. The first radiation capacity may be greater than the second radiation capacity. The first radiation capacity may be lesser than the second radiation capacity. The first radiation capacity may be greater, on a per-unit-length-of-device basis, than the second radiation capacity. The first radiation capacity may be lesser, on a per-unit-length-of-device basis, than the second radiation capacity.

The chamber may be part of a barrel of a prefilled syringe.

The apparatus may include an envelope. The envelope may sterilely surround the chamber. The envelope may sterilely surround the delivery assembly. The envelope may sterilely surround the fluid-displacement member. The envelope may be an envelope that encloses no residue. The residue may be a residue from chemical sterilization.

The chamber may include glass. The glass may include a borosilicate glass. The chamber may include polymer. Table 5 lists selected illustrative materials that may be included in the chamber.

TABLE 5

Selected illustrative materials that may be included in the chamber.

| Selected illustrative materials |
| --- |
| Glass |
| Borosilicate glass |
| Polyethylene |
| Polypropylene |
| Polycarbonate |

TABLE 5-continued

Selected illustrative materials that may be included in the chamber.

| Selected illustrative materials |
| --- |
| Cyclic olefins |
| Polyesters, for example, polyethylene terephthalate |
| Acrylonitrile butadiene styrene |
| Polyoxymethylene |
| Any other suitable materials |

The outlet may have a central axis that extends away from the chamber. The delivery assembly may be a delivery assembly that is not rotationally symmetric about the axis. The delivery assembly may be arranged along an axis that is not collinear with the central axis.

The delivery assembly may include an autoinjector. The chamber may include a reservoir of the autoinjector.

The medicament may include a molecule. The molecule may have a mass. The mass may be in a range. The range may have a lower value and an upper limit. The lower and upper limits may be included in the range. Table 6 lists selected illustrative lower and upper limits.

TABLE 6

Selected illustrative lower and upper limits, Dalton ("Da").

| Lower | Upper |
| --- | --- |
| 0 | 3,000 |
| 2,800 | 3,000 |
| 3,000 | 3,200 |
| 3,200 | 3,400 |
| 3,400 | 3,600 |
| 3,600 | 3,800 |
| 3,800 | 4,000 |
| 4,000 | 5,000 |
| 5,000 | 6,000 |
| 6,000 | 8,000 |
| 8,000 | 10,000 |
| 10,000 | 15,000 |
| 15,000 | 20,000 |
| 20,000 | 25,000 |
| 25,000 | 40,000 |
| 40,000 | 50,000 |
| 50,000 | 60,000 |
| 60,000 | 100,000 |
| 100,000 | 125,000 |
| 125,000 | 150,000 |
| 150,000 | 175,000 |
| 175,000 | 200,000 |
| 200,000 | 225,000 |
| 225,000 | 250,000 |
| 250,000 | 500,000 |
| 500,000 | — |

The medicament may include a molecule that has a mass that is not greater than 3,000 Dalton.

The medicament may include a molecule that has a mass that is in the range 2,800 Dalton to 3,000 Dalton.

The medicament may include a molecule that has a mass that is not less than 3,000 Dalton and not more than 3,200 Dalton.

The medicament may include a molecule that has a mass that is not less than 3,200 Dalton and not more than 3,400 Dalton.

The medicament may include a molecule that has a mass that is not less than 3,400 Dalton and not more than 3,600 Dalton.

The medicament may include a molecule that has a mass that is not less than 3,600 Dalton and not more than 3,800 Dalton.

The medicament may include a molecule that has a mass that is not less than 3,800 Dalton and not more than 4,000 Dalton.

The medicament may include a molecule that has a mass that is not less than 4,000 Dalton and not more than 5,000 Dalton.

The medicament may include a molecule that has a mass that is not less than 5,000 Dalton and not more than 6,000 Dalton.

The medicament may include a molecule that has a mass that is not less than 6,000 Dalton and not more than 8,000 Dalton.

The medicament may include a molecule that has a mass that is not less than 8,000 Dalton and not more than 10,000 Dalton.

The medicament may include a molecule that has a mass that is not less than 10,000 Dalton and not more than 15,000 Dalton.

The medicament may include a molecule that has a mass that is not less than 15,000 Dalton and not more than 20,000 Dalton.

The medicament may include a molecule that has a mass that is not less than 20,000 Dalton and not more than 25,000 Dalton.

The medicament may include a molecule that has a mass that is not less than 25,000 Dalton and not more than 40,000 Dalton.

The medicament may include a molecule that has a mass that is not less than 40,000 Dalton and not more than 50,000 Dalton.

The medicament may include a molecule that has a mass that is not less than 50,000 Dalton and not more than 60,000 Dalton.

The medicament may include a molecule that has a mass that is not less than 60,000 Dalton and not more than 100,000 Dalton.

The medicament may include a molecule that has a mass that is not less than 100,000 Dalton and not more than 125,000 Dalton.

The medicament may include a molecule that has a mass that is not less than 125,000 Dalton and not more than 150,000 Dalton.

The medicament may include a molecule that has a mass that is not less than 150,000 Dalton and not more than 175,000 Dalton.

The medicament may include a molecule that has a mass that is not less than 175,000 Dalton and not more than 200,000 Dalton.

The medicament may include a molecule that has a mass that is not less than 200,000 Dalton and not more than 225,000 Dalton.

The medicament may include a molecule that has a mass that is not less than 225,000 Dalton and not more than 250,000 Dalton.

The medicament may include a molecule that has a mass that is not less than 250,000 Dalton and not more than 500,000 Dalton.

The medicament may include a molecule that has a mass that is not less than 500,000 Dalton.

The medicament may include a molecule that has a mass that is not less than 3,000 Dalton and not more than 500,000 Dalton.

The medicament may include a protein.

The medicament may include a sugar. The sugar may include a monosaccharide. The sugar may include a disaccharide. The sugar may include sucrose (mol. weight 342 gram/mol). The sugar may include trehalose (mol. weight 342 gram/mol). The sugar may include glucose (mol. weight 180 gram/mol). The sugar may include mannitol (182 gram/mol). The sugar may include sorbitol (182 gram/mol). The sugar may include lactose (342 gram/mol). The sugar may include maltose (342 gram/mol).

The medicament may include an antibody. The antibody may have a mass that is about 150 kDa. The antibody may have a mass that is in a range from about 140 kDa to about 160 kDa. The antibody may have a mass that is no more than 140 kDA. The antibody may have a mass that is no less than 160 kDa. The antibody may include a monoclonal antibody.

The medicament may include an antibody fragment. The fragment may have a mass that is about 50 kDa. The fragment may have a mass that is in a range from about 40 kDa to about 60 kDa. The fragment may have a mass that is no more than 40 kDA. The fragment may have a mass that is no less than 60 kDa.

The medicament may include a peptide therapeutic. The peptide may have a mass that is about 10 kDa. The peptide therapeutic may have a mass that is in a range from about 8 kDa to about 12 kDa. The peptide therapeutic may have a mass that is no more than 8 kDA. The peptide therapeutic may have a mass that is no less than 12 kDa.

The medicament may include a biological product. The biological product may be alive. The biological product may be a biological product that is not alive. Table 7 lists selected illustrative biological products.

TABLE 7

Selected illustrative biological products.

A vaccine
A blood element
Blood
An allergenic
A cell
An organelle
A gene

The medicament may include a formulation of one or more compounds. The compounds may include naturally occurring substances. The compounds may include substances derived from naturally occurring substances. The compounds may include synthetically produced substances. The compounds may include chimeric substances. The compounds may include engineered substances. The compounds may include humanized substances. The compounds may include substances produced by recombinant techniques. The compounds may include substances modified by recombinant techniques. The medicament may include material in a lyophilized state. The medicament may include material for reconstitution of a lyophilized material.

The compounds may include a drug accepted for therapeutic treatment of a patient. The compounds may include a substance used in a therapeutic protocol. The compounds may include a substance used in a diagnostic protocol. The compounds may include a substance used in an experimental protocol. The compounds may include a substance compatible for use with apparatus and methods of the invention.

The medicament may include any medical agent listed herein, either alone or in combination with one or more other listed medical agents or with one or more other, non-listed, medical agents. The medical agents may include anti-glaucoma medications, other ocular agents, neuroprotective agents, antimicrobial agents, anti-inflammatory agents (including steroids and non-steroidal compounds), and biological agents including hormones, enzymes or enzyme-related components, antibodies or antibody-related components, oligonucleotides (including DNA, RNA, short-interfering RNA, and other suitable oligonucleotides, such as antisense oligonucleotides), DNA/RNA vectors, viruses or viral vectors, peptides, and proteins. The medical agents may include anti-angiogenesis agents, including angiostatin, anecortave acetate, thrombospondin, vascular endothelial growth factor (VEGF) receptor tyrosine kinase inhibitors, and anti-VEGF drugs, such as ranibizumab (LUCENTIS®), bevacizumab (AVASTIN®), pegaptanib (MACUGEN®), sunitinib, and sorafenib, and any of a variety of known small-molecule and transcription inhibitors having an anti-angiogenesis effect; ophthalmic drugs, including glaucoma agents, such as adrenergic antagonists, including beta-blocker agents such as atenolol, propranolol, metipranolol, betaxolol, carteolol, levobetaxolol, levobunolol and timolol. The medical agents may include platelet-derived growth factor (PDGF) inhibitors and anti-PDGF drugs. The medical agents may include transformation growth factor (TGF) inhibitors and anti-TGF drugs. The medical agents may include anti-inflammatory agents including glucocorticoids and corticosteroids, such as betamethasone, cortisone, dexamethasone, dexamethasone 21-phosphate, methylprednisolone, prednisolone 21-phosphate, prednisolone acetate, prednisolone, loteprednol, medrysone, fluocinolone acetonide, triamcinolone acetonide, triamcinolone, beclomethasone, budesonide, flunisolide, fluorometholone, fluticasone, hydrocortisone, hydrocortisone acetate and rimexolone; and non-steroidal anti-inflammatory agents including diclofenac, flurbiprofen, ibuprofen, bromfenac, nepafenac, ketorolac, salicylate, indomethacin, naxopren, naproxen, piroxicam and nabumetone. The medical agents may include anti-cytokine agents; the medical agents may include anti-interleukin-6 agents such as tocilizumab (ACTEMRA®). The medical agents may include anti-complement agents, including those targeting complement factor D (such as an anti-complement factor D antibody or an antigen-binding fragment thereof) such as lampalizumab, and those targeting complement factor H (such as an anti-complement factor H antibody or an antigen-binding fragment thereof). The medical agents may include angiopoietin-specific agents, such as an angiopoietin-2 antibody or an antigen-binding fragment thereof. The medical agents may include human growth hormone. The medical agents may include any suitable medical agent.

The medicament may include one or more derivatives of any of the above-mentioned medical agents. The medicament may include advanced forms of any of the above-mentioned medical agents. The medicament may include mutated forms of any of the above-mentioned medical agents. The medicament may include combinations of any of the above-mentioned medical agents. The combinations may be incorporated into a multi-specific molecule. The multi-specific molecule may exhibit properties of its constituent parts. The multi-specific molecule may exhibit properties different from any if its constituent parts. The medicament may include depots, hydrogels and pegylated forms of any of the above medical agents. The medicament may include any suitable form of any of the above medical agents.

The envelope may include a sleeve.

The envelope may include a radiation detector.

The envelope may include an interior atmosphere. The interior atmosphere may be enriched, relative to an exterior atmosphere exterior and adjacent to the envelope, in an inert gas. The exterior atmosphere may be that of a sterile field. The exterior atmosphere may be that of a health care facility. The exterior atmosphere may be that of a patient examination room. The inert gas may include nitrogen, $N_2$. The inert gas may include Argon. The inert gas may include Helium. The inert gas may include a noble gas. The inert gas may include any suitable gas.

The envelope may enclose a water-absorbing compound at a concentration that is greater than a concentration of the compound exterior and adjacent to the envelope.

A concentration of gaseous oxygen, $O_2$, enclosed in the envelope, may be a concentration that is no greater than 50 parts per million. The concentration of gaseous oxygen may be a concentration that is no greater than 40 parts per million. The concentration of gaseous oxygen may be a concentration that is no greater than 30 parts per million. The concentration of gaseous oxygen may be a concentration that is no greater than 20 parts per million. The concentration of gaseous oxygen may be a concentration that is no greater than 10 parts per million. The concentration of gaseous oxygen may be a concentration that is no greater than 1 parts per million. The concentration of gaseous oxygen may be a concentration that is no greater than 0.5 parts per million. The concentration of gaseous oxygen may be a concentration that is no greater than 0.1 parts per million. The concentration of gaseous oxygen may be a concentration that is no greater than 0.001 parts per million.

A concentration of gaseous water vapor, $H_2O$, enclosed in the envelope, may be a concentration that is no greater than 50 parts per million. The concentration of gaseous water vapor may be a concentration that is no greater than 40 parts per million. The concentration of gaseous water vapor may be a concentration that is no greater than 30 parts per million. The concentration of gaseous water vapor may be a concentration that is no greater than 20 parts per million. The concentration of gaseous water vapor may be a concentration that is no greater than 10 parts per million. The concentration of gaseous water vapor may be a concentration that is no greater than 1 parts per million. The concentration of gaseous water vapor may be a concentration that is no greater than 0.5 parts per million. The concentration of gaseous water vapor may be a concentration that is no greater than 0.1 parts per million. The concentration of gaseous water vapor may be a concentration that is no greater than 0.001 parts per million.

The envelope may include a first impermeable member. The first impermeable member may be impermeable to mass transfer. The envelope may include a second impermeable member. The second impermeable member may be impermeable to mass transfer. The second impermeable member may be disposed opposite the first impermeable member. The first and second impermeable members may be sealed to each other. The first and second impermeable members may define a cabinet.

One or both of the impermeable members may have a permeability to $H_2O$ that is sufficiently low that the water-absorbing compound remains unsaturated for a shelf-life period. The shelf-life period may be no less than 1 day. The shelf-life period may be no less than 10 days. The shelf-life period may be no less than 100 days. The shelf-life period may be no less than 500 days. The shelf-life period may be no less than 1000 days. The shelf-life period may be no less than 2000 days.

One or both of the impermeable members may have a permeability to $O_2$ that is sufficiently low that the water-absorbing compound remains unsaturated for a shelf-life period. The shelf-life period may be no less than 1 day. The shelf-life period may be no less than 10 days. The shelf-life period may be no less than 100 days. The shelf-life period may be no less than 500 days. The shelf-life period may be no less than 1000 days. The shelf-life period may be no less than 2000 days.

The first impermeable member may be recessed to accommodate the delivery assembly. The recess may be formed by molding the first impermeable member.

The first impermeable member may include a polymer. The polymer may include a molded polymer.

The second impermeable member may include a foil. The foil may be a packaging foil. The foil may be a foil such as that available under the trademark TYVEK from E. I. du Pont de Nemours and Company, Wilmington, Del., and its affiliates. The foil may be a foil such as that available under the trademark OVANTEX from Oliver-Tolas, Feasterville, Pa., and its affiliates.

The foil may include paper. The foil may include cellulose. The foil may include metal. The foil may include polyethylene, for example, high density polyethylene, which may be available under the tradename TYVEK, polyester or any other suitable plastic.

The first impermeable member may include a foil and the second impermeable member may include a foil.

The first impermeable member may be recessed to accommodate the delivery assembly. The second impermeable member may be recessed to accommodate the delivery assembly.

The first impermeable member may include a sheath. The second impermeable member may include a cap. The cap may include a foil.

The envelope may include a blister pack.

The residue may include vapor. The residue may include an adsorbed molecule. The adsorbed molecule may be disposed on the envelope. The adsorbed molecule may be disposed on the delivery assembly. The adsorbed molecule may be disposed on a surface of the chamber.

The first radiation capacity may be greater than the second radiation capacity by a multiple. The second radiation capacity may be greater than the first radiation capacity by a multiple. The numerical value of the multiple may be defined by a single-sided lower limit. The numerical value may be defined by a double-sided range having a lower limit and an upper limit. Table 8 shows selected illustrative single-sided lower limits and ranges having lower and upper limits.

TABLE 8

Selected illustrative single-sided lower limits and ranges having lower and upper limits.

| Illustrative multiple (single-sided lower limit) | Illustrative range of multiple (double-sided: lower and upper range) | |
| --- | --- | --- |
| | Lower | Upper |
| 1.0 | 1.0 | 1.2 |
| 1.2 | 1.2 | 1.3 |
| 1.3 | 1.3 | 1.4 |
| 1.4 | 1.4 | 1.5 |
| 1.5 | 1.5 | 1.6 |
| 1.6 | 1.6 | 1.7 |
| 1.7 | 1.7 | 1.8 |
| 1.8 | 1.8 | 1.9 |
| 1.9 | 1.9 | 2.0 |
| 2.0 | 2.0 | 3.0 |
| 3.0 | 3.0 | 4.0 |
| 4.0 | 4.0 | 5.0 |
| 5.0 | 5.0 | 7.0 |
| 7.0 | 7.0 | 10.0 |
| 10.0 | 10.0 | 15.0 |

TABLE 8-continued

Selected illustrative single-sided lower limits and ranges having lower and upper limits.

| Illustrative multiple (single-sided lower limit) | Illustrative range of multiple (double-sided: lower and upper range) | |
| --- | --- | --- |
| | Lower | Upper |
| 15.0 | 15.0 | 20.0 |
| 20.0 | 20.0 | 50.0 |
| 50.0 | 50.0 | 75.0 |
| 75.0 | 75.0 | 100.0 |
| 100.0 | 100.0 | 125.0 |
| 125.0 | 125.0 | 140.0 |
| 140.0 | 140.0 | 150.0 |
| 150.0 | 150.0 | 175.0 |
| 175.0 | 175.0 | 200.0 |
| 200.0 | 200.0 | 1000.0 |

The first attenuation capacity may be greater than the second attenuation capacity by a multiple that is greater than 1.0.

The first attenuation capacity may be greater than the second attenuation capacity by a multiple that is greater than 1.2.

The first attenuation capacity may be greater than the second attenuation capacity by a multiple that is greater than 1.3.

The first attenuation capacity may be greater than the second attenuation capacity by a multiple that is greater than 1.4.

The first attenuation capacity may be greater than the second attenuation capacity by a multiple that is greater than 1.5.

The first attenuation capacity may be greater than the second attenuation capacity by a multiple that is greater than 1.6.

The first attenuation capacity may be greater than the second attenuation capacity by a multiple that is greater than 1.7.

The first attenuation capacity may be greater than the second attenuation capacity by a multiple that is greater than 1.8.

The first attenuation capacity may be greater than the second attenuation capacity by a multiple that is greater than 1.9.

The first attenuation capacity may be greater than the second attenuation capacity by a multiple that is greater than 2.0.

The first attenuation capacity may be greater than the second attenuation capacity by a multiple that is greater than 3.0.

The first attenuation capacity may be greater than the second attenuation capacity by a multiple that is greater than 4.0.

The first attenuation capacity may be greater than the second attenuation capacity by a multiple that is greater than 5.0.

The first attenuation capacity may be greater than the second attenuation capacity by a multiple that is greater than 7.0.

The first attenuation capacity may be greater than the second attenuation capacity by a multiple that is greater than 10.0.

The first attenuation capacity may be greater than the second attenuation capacity by a multiple that is greater than 15.0.

The first attenuation capacity may be greater than the second attenuation capacity by a multiple that is greater than 20.0.

The first attenuation capacity may be greater than the second attenuation capacity by a multiple that is greater than 50.0.

The first attenuation capacity may be greater than the second attenuation capacity by a multiple that is greater than 75.0.

The first attenuation capacity may be greater than the second attenuation capacity by a multiple that is greater than 100.0.

The first attenuation capacity may be greater than the second attenuation capacity by a multiple that is greater than 125.0.

The first attenuation capacity may be greater than the second attenuation capacity by a multiple that is greater than 140.0.

The first attenuation capacity may be greater than the second attenuation capacity by a multiple that is greater than 150.0.

The first attenuation capacity may be greater than the second attenuation capacity by a multiple that is greater than 175.0.

The first attenuation capacity may be greater than the second attenuation capacity by a multiple that is greater than 200.0.

The envelope may have a third radiation capacity.

The first radiation capacity may be greater than the third radiation capacity. The first radiation capacity may be greater, per unit length along a longitudinal axis of the apparatus, than the third radiation capacity. The first radiation capacity may be greater than the third radiation capacity by a multiple having a value such as one of those shown in Table 8.

The third radiation capacity may be greater than the first radiation capacity. The third radiation capacity may be greater, per unit length along a longitudinal axis of the apparatus, than the first radiation capacity. The third radiation capacity may be greater than the first radiation capacity by a multiple having a value such as one of those shown in Table 8.

The delivery assembly mass may include a toroidal element. The toroidal element may be disposed about the longitudinal axis. The delivery assembly may include a shaft element. The shaft element may be disposed along the longitudinal axis. The toroidal element may be rotatable, about the longitudinal axis, relative to the shaft. The shaft may be displaceable along the longitudinal axis. The shaft may be engaged with a plunger to move medicament within the chamber. The shaft may be engaged with the plunger to move medicament out of the chamber.

The apparatus may include a sheath. The chassis may support the sheath. The chamber may support the sheath. The sheath may be disposed about the medicament. The sheath may be disposed about the chamber. The sheath may have a fourth radiation capacity. The first radiation capacity may be greater, per unit length along a longitudinal axis of the apparatus, than the fourth radiation capacity. The first radiation capacity may be greater than the fourth radiation capacity by a multiple having a value such as one of those shown in Table 8.

Methods for providing the apparatus are provided.

The method may include delivering, using an electron beam, to the outer surface of a barrel of the chamber, a predetermined dose of radiation. The sterilizing may include applying a predetermined dose to a surface of the delivery assembly. The surface may be a surface interior the delivery assembly. The surface may be a surface of an element of the delivery assembly. The surface may be a surface of the chassis. The surface may be a surface of the fluid-displacement member. The methods may deliver different doses to different parts of the delivery assembly. The methods may deliver the same doses to different parts of the delivery assembly. The methods may deliver different doses to different parts of the chamber. The methods may deliver the same doses to different parts of the chamber. The methods may deliver the same dose to a part of the delivery assembly and a part of a chamber.

Table 9 shows selected illustrative single-sided upper limits and ranges having lower and upper limits.

TABLE 9

Selected illustrative single-sided upper limits and ranges having lower and upper limits.

| Illustrative dose, kiloGray (KGy) (single-sided upper limit) | Illustrative range of multiple (double-sided: lower and upper range) | |
|---|---|---|
| | Lower | Upper |
| | 0 | 2.0 |
| 2.0 | 2.0 | 2.5 |
| 2.5 | 2.5 | 5.0 |
| 5.0 | 5.0 | 7.5 |
| 7.5 | 7.5 | 10.0 |
| 10.0 | 10.0 | 12.0 |
| 12.0 | 12.0 | 14.0 |
| 14.0 | 14.0 | 16.0 |
| 16.0 | 16.0 | 20.0 |
| 20.0 | 20.0 | 22.0 |
| 22.0 | 22.0 | 24.0 |
| 24.0 | 24.0 | 26.0 |
| 26.0 | 26.0 | 28.0 |
| 28.0 | 28.0 | 30.0 |
| 30.0 | 30.0 | 32.0 |
| 32.0 | 32.0 | 34.0 |
| 34.0 | 34.0 | 36.0 |
| 36.0 | 36.0 | 38.0 |
| 38.0 | 38.0 | 40.0 |
| 40.0 | 40.0 | 50.0 |
| 50.0 | 50.0 | 75.0 |
| 75.0 | 75.0 | 100.0 |
| 100.0 | 100.0 | 120.0 |
| 120.0 | 120.0 | 125.0 |
| 125.0 | 125.0 | 150.0 |
| 150.0 | 150.0 | 175.0 |
| 175.0 | 175.0 | 200.0 |
| 200. | 200.0 | 250.0 |

The method may include sterilizing the delivery assembly when the delivery assembly is affixed to the chamber. The sterilizing may be performed when the delivery assembly and the chamber are affixed to each other and sealed inside the envelope.

The sterilizing may be performed when the delivery assembly and the chamber are affixed to each other, the medicament is in the chamber, and the delivery assembly and the chamber are sealed inside the envelope. The sterilizing may include directing the electron beam through the envelope.

The method may include providing a radiation shield to protect the medicament from the electronic beam. The radiation shield may protect the medicament from the e-beam. The radiation shield may protect the medicament from Bremsstrahlung radiation.

The sterilizing may include magnetically steering the electron beam. The steering may include focusing the beam. The steering may include panning the beam to apply the dosage across a region of the apparatus. The steering may include tilting the beam to apply the dosage across a region of the apparatus. The steering may include rasterizing the beam to apply the dosage across a region of the apparatus. The sterilizing may include providing a magnetic radiation trap to localize radiation away from the medicament.

Figure 10:
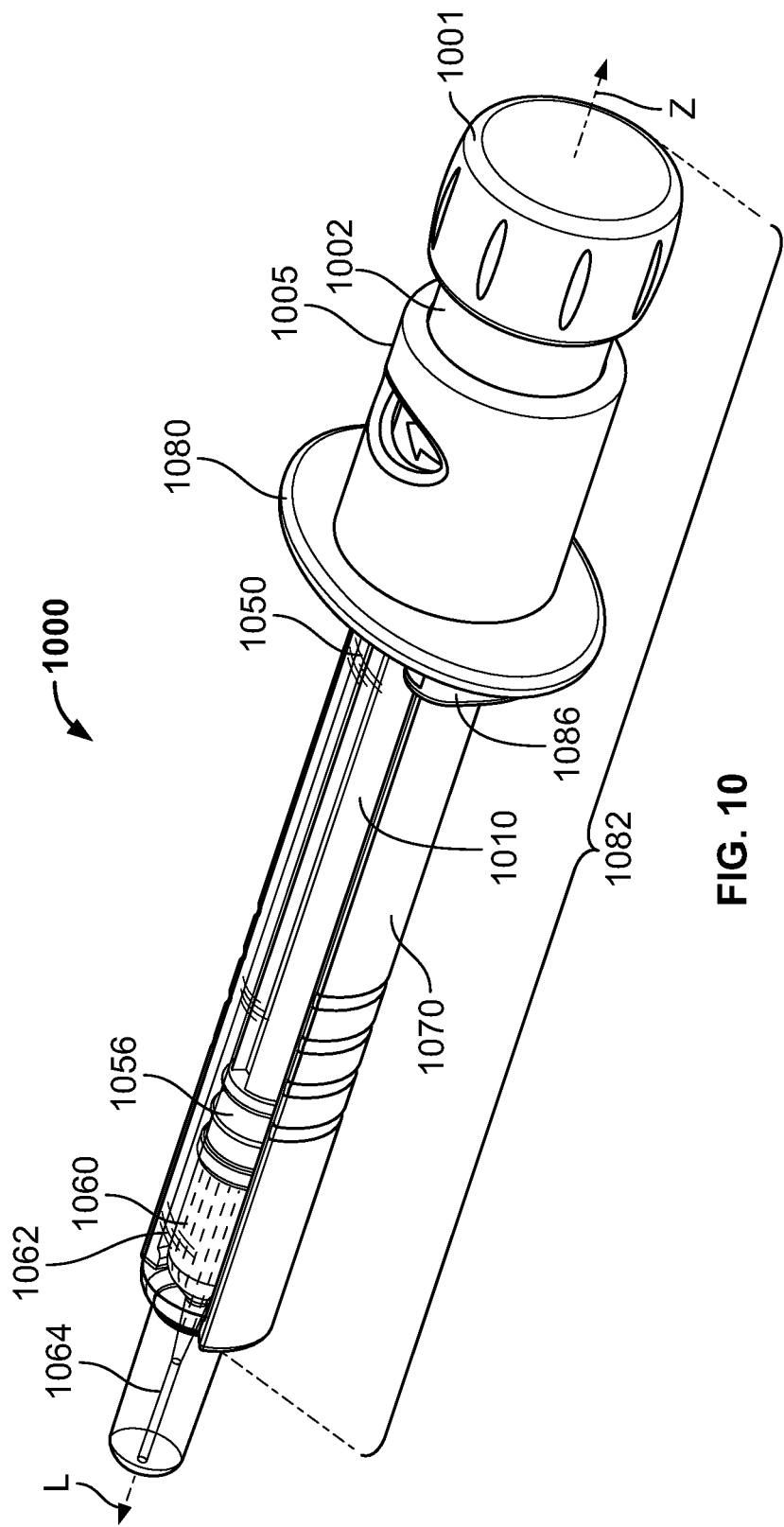
FIG. 10 shows a perspective view of illustrative apparatus in accordance with principles of the invention.

FIG. 10 shows illustrative apparatus 1000 for delivering medicament.

Apparatus 1000 may define longitudinal axis L. Axis L may be collinear with direction z. Apparatus 1000 is shown in a state in which apparatus 1000 is fully assembled. In that state, apparatus 1000 may be ready for priming. In that state, apparatus 1000 may be ready for transformation of medicament for delivery. In that state, apparatus 1000 may be ready to discharge the medicament. In that state, discharge of the medicament from apparatus 1000 may not have begun.

Apparatus 1000 may include a fluid-displacement member such as plunger rod 1010. Rod 1010 may be part of a mixing configuration (not shown), for example, for reconstituting a medicament.

Apparatus 1000 may include medicament container 1050. Container 1050 may be part of the mixing configuration (not shown). Container 1050 may be disposed coaxial with axis L. Container 1050 may be cylindrical, partially cylindrical or have any other suitable form. A distal portion of rod 1010 may be disposed within container 1050.

Container 1050 may contain medicament 1060 in chamber 1062. Outlet 1064 may have a central axis (illustrated collinear with L) that extends away from chamber 1062. Container 1050 may be in sealed engagement with plunger 1056. A distal end of rod 1010 may abut a proximal surface of plunger 1056. Rod 1010 may engage plunger 1056 such that it can push or pull plunger 1056. Rod 1010 may contact plunger 1056 such that it can push, but not pull, plunger 1056.

Apparatus 1000 may include delivery assembly 1082. Delivery assembly 1082 may include chassis 1086. Chassis 1086 may engage container 1050. Chassis 1086 may support one or more elements of delivery assembly 1082 in a corresponding fixed position along axis L. Plunger 1056 may be engaged with delivery assembly 1082. Plunger 1056 may be movable along axis L. One or more elements of delivery assembly 1082 may be fixed longitudinally along and rotatable about axis L.

Container 1050 may be considered to be not part of delivery assembly 1082.

Delivery assembly 1082 may include proximal knob 1002. Knob 1002 may be disposed coaxial with axis L. Grip 1001 may be provided on knob 1002. Knob 1002 may be threadingly attached to rod 1010.

Delivery assembly 1082 may include device housing 1070. Housing 1070 may be disposed coaxial with axis L. Housing 1070 may be cylindrical, partially cylindrical or have any other suitable form.

Delivery assembly 1082 may include finger flange 1080. Finger flange 1080 may be separate from housing 1070. Finger flange 1080 may be attached to housing 1070. Finger flange 1080 may be monolithic with housing 1070.

Delivery assembly 1082 may include collar 1005. Collar 1005 may be disposed coaxial with axis L. Collar 1005 may be cylindrical, partially cylindrical or have any other suitable form. Collar 1005 may be attached to finger flange 1080. Collar 1005 may be monolithic with finger flange 1080. Collar 1005 may be attached to housing 1070. Collar 1005 may be monolithic with housing 1070.

Figure 11:
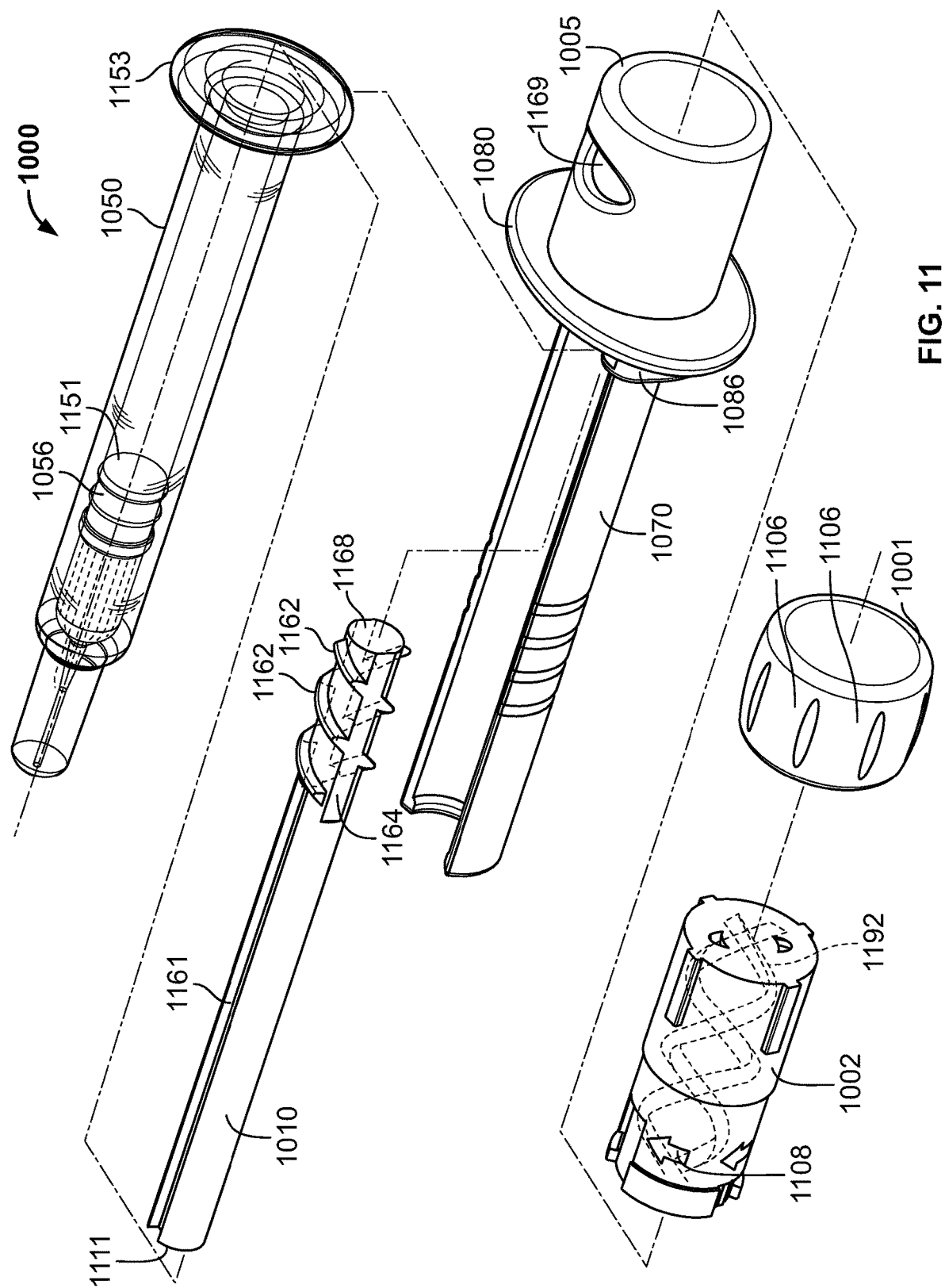
FIG. 11 shows an exploded, perspective view of apparatus shown in FIG. 10.

FIG. 11 shows knob 1002. Knob 1002 may include threads 1192 (shown in phantom) internal to knob 1002.

Grip 1001 may contribute to traction on knob 1002 for effecting longitudinal translation of rod 1010. Grip 1001 may contribute to ergonomic finger contact of the operator with knob 1002 for effecting longitudinal translation of rod 1010. The finger contact with knob 1002 through grip 1001 may conduct tactile feedback to the operator of an extent of distal longitudinal translation of rod 1010 along axis L.

Knob 1002 may include turn ridges 1106. Turn ridges 1106 may be utilized by the operator to effect rotation of knob 1002 about axis L. Turn ridges 1106 may contribute to traction on knob 1002 for effecting translation of rod 1010. Turn ridges 1106 may contribute to ergonomic finger contact of the operator with knob 1002 for effecting translation of rod 1010 through rotation of knob 1002. The finger contact with turn ridges 1106 may conduct tactile feedback to the operator of an extent of translation of rod 1010 along axis L.

Turn ridges 1106 may be spaced circumferentially around knob 1002. Turn ridges 1106 may be spaced regularly around a circumference of grip 1001. Turn ridges 1106 being spaced regularly about the circumference of grip 1001 may provide the operator a measure of an extent of rotation performed.

Knob 1002 may include turn direction signage 1108. In the operational state, apparatus 1000 may effect distal displacement of rod 1010 within container 1050 in response to rotation of knob 1002 about axis L in only one of two rotational directions. Turn direction signage 1108 may provide the operator with cues as to an effective rotational direction. The cues may serve as reminders before and/or during the operational state. The cues may be visual. The cues may be tactile.

As depicted, the effective rotational direction for distal displacement of rod 1010 within container 1050 in response to rotation of knob 1002 about axis L may be clockwise for apparatus 1000. (For some embodiments, not shown, counter-clockwise rotation may the effective rotational direction. For some embodiments, turn direction signage may provide cues for counter-clockwise rotation.)

Distal rod end 1111 may define a distal end of anti-rotation slot 1161. Anti-rotation slot 1161 may be parallel to axis L. Distal rod end 1111 may include one or more additional anti-rotation slots or features (not shown) distributed about the circumference of rod 1010 in a regular or irregular manner. Anti-rotation slot 1161 may extend all or some of the way proximally to threads 1162. Threads 1162 may extend proximally some or all of the way to proximal rod end 1168. Threads 1162 may engage threads 1192 of knob 1002.

Rod 1010 may include flat face 1164. Flat face 1164 may be parallel to axis L. Rod 1010 may include one or more additional flat faces (not shown) distributed about the circumference of rod 1010 in a regular or irregular manner. Flat face 1164 may extend all or some of the way from near anti-rotation slot 1161 to proximal end 1168. Flat face 1164 may be longitudinally coextensive with threads 1162. Flat face 1164 may be circumferentially displaced from slot 1161. The circumferential displacement may be 100° of arc from slot 1161.

Container 1050 may be disposed in device 1000 distal to finger flange 1080. Container 1050 may be disposed in housing 1070 distal to finger flange 1080. Proximal rim 1153 of container 1050 surrounding a proximal opening of container 1050 may be recessed in device 1000 distal to finger flange 1080. Proximal rim 1153 of container 1050 may be recessed in housing 1070.

Knob 1002 may be disposed coaxially within collar 1005. Collar 1005 may include viewing window 1169. A portion of signage 1108 may be visible through window 1169.

Rod 1010 may be contained in container 1050 with distal end 1111 abutting plunger proximal face 1151. Proximal rod end 1168 may extend proximally into collar 1005. Knob 1002 may extend distally into collar 1005 to threadingly engage rod 1010.

Figure 12:
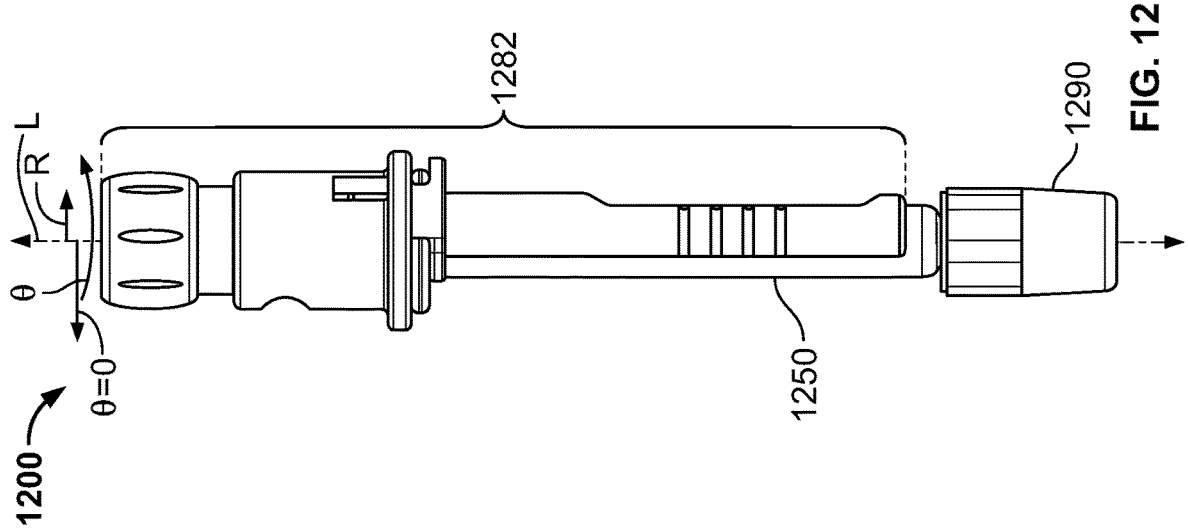
FIG. 12 shows a view of illustrative apparatus in accordance with principles of the invention.

FIG. 12 shows illustrative apparatus 1200 for delivering medicament. Apparatus 1200 may include delivery assembly 1282. Apparatus 1200 may include container 1250. Container 1250 may be considered to not be part of delivery assembly 1282. Apparatus 1200 may include hub 1290. Hub 1290 may be affixed to container 1250. Hub 1290 may be a needle hub.

Figure 13:
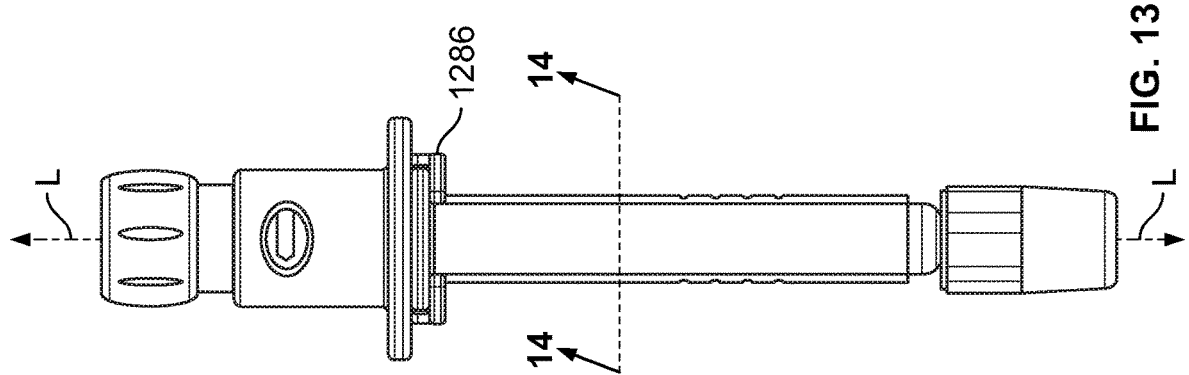
FIG. 13 shows another view of apparatus shown in FIG. 12.

FIG. 13 shows illustrative apparatus 1200 from a perspective that is different from that shown in FIG. 12.

Figure 14:
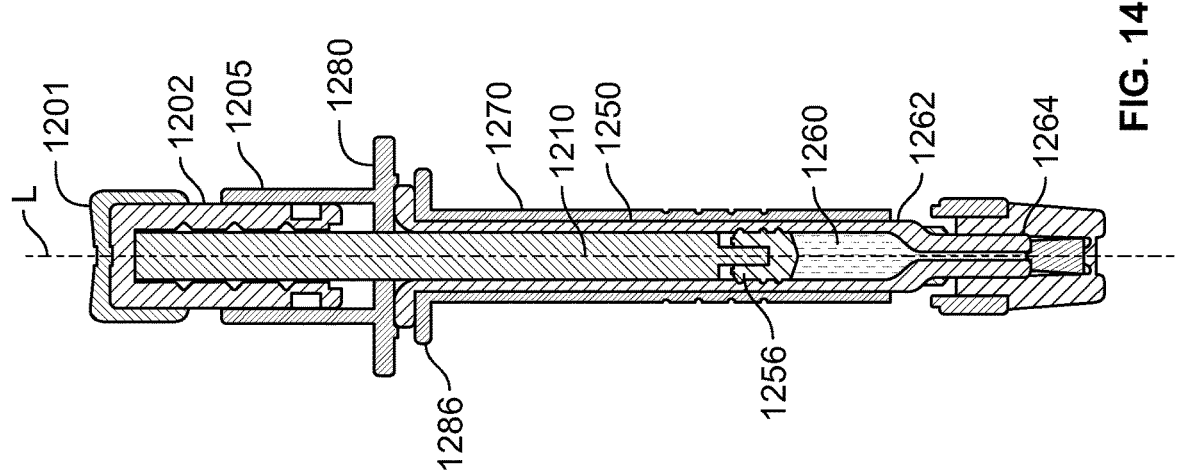
FIG. 14 shows a cross-sectional view of apparatus shown in FIG. 13, the view taken along lines 14-14 (shown in FIG. 13)

FIG. 14 shows a cross-sectional view of apparatus 1200 taken along lines 14-14 (shown in FIG. 13).

Apparatus 1200 may define longitudinal axis L. Axis L may be collinear with direction z. Apparatus 1200 is shown in a state in which apparatus 1200 is fully assembled. In that state, apparatus 1200 may be ready for priming. In that state, apparatus 1200 may be ready for transformation of the medicament for delivery. In that state, apparatus 1200 may be ready to discharge the medicament. In that state, discharge of the medicament from apparatus 1200 may not have begun.

Apparatus 1200 may include a fluid-displacement member such as plunger rod 1210. Rod 1210 may be part of a mixing configuration (not shown), for example, for reconstituting a medicament.

Container 1250 may be part of the mixing configuration (not shown). Container 1250 may be disposed coaxial with axis L. Container 1250 may be cylindrical, partially cylindrical or have any other suitable form. A distal portion of rod 1210 may be disposed within container 1250.

Container 1250 may contain medicament 1260 in chamber 1262. Outlet 1264 may have a central axis (illustrated as collinear with L) that extends away from chamber 1262. Container 1250 may be in sealed engagement with plunger 1256. A distal end of rod 1210 may abut a proximal surface of plunger 1256. A distal end of rod 1210 may engage a proximal surface of plunger 1256. Rod 1210 may engage plunger 1256 such that it can push or pull plunger 1256. Rod 1210 may contact plunger 1256 such that it can push, but not pull, plunger 1256.

Delivery assembly 1282 may include chassis 1286. Chassis 1286 may engage container 1250. Chassis 1286 may support one or more elements of delivery assembly 1282 in a corresponding fixed position along axis L. Plunger 1256 may be engaged with delivery assembly 1282. Plunger 1256 may be movable along axis L. One or more elements of delivery assembly 1282 may be fixed longitudinally along and rotatable about axis L.

Delivery assembly 1282 may include proximal knob 1202. Knob 1202 may be disposed coaxial with axis L. Grip 1201 may be provided on knob 1202. Knob 1202 may be threadingly attached to rod 1210.

Delivery assembly 1282 may include device housing 1270. Housing 1270 may be disposed coaxial with axis L. Housing 1270 may be cylindrical, partially cylindrical or have any other suitable form.

Delivery assembly 1282 may include finger flange 1280. Finger flange 1280 may be separate from housing 1270. Finger flange 1280 may be attached to housing 1270. Finger flange 1280 may be monolithic with housing 1270. Finger flange 1280 may be monolithic with chassis 1286.

Delivery assembly 1282 may include collar 1205. Collar 1205 may be disposed coaxial with axis L. Collar 1205 may be cylindrical, partially cylindrical or have any other suitable form. Collar 1205 may be attached to finger flange 1280. Collar 1205 may be monolithic with finger flange 1280. Collar 1205 may be attached to housing 1270. Collar 1205 may be monolithic with housing 1270. Collar 1205 may be attached to chassis 1286. Collar 1205 may be monolithic with chassis 1286.

FIG. 15 shows illustrative envelope 1500. Envelope 1500 may enclose some or all of an apparatus such as an apparatus having one or more features of the illustrative concepts shown in one or more of FIGS. 1-8 or an apparatus having one or more features in common with the illustrative apparatus show in one or more of FIGS. 10-14. Envelope 1500 may enclose an atmosphere.

Envelope 1500 may include sleeve 1502. Sleeve 1502 may be hollow. Sleeve 1502 may include first section 1504. Sleeve 1502 may include second section 1506. First section 1504 may have a diameter that is greater than that of second section 1506. First section 1504 may accommodate a large-diameter portion of the apparatus. Second section 1506 may accommodate a relatively smaller-diameter portion of the apparatus.

Envelope 1500 may include foil or cap 1508. Foil or cap 1508 may be sealed to sleeve 1502. Envelope 1500, with the enclosed apparatus, may be sterilized after foil or cap 1508 is sealed to sleeve 1502.

FIG. 16 shows that sleeve 1502 may include illustrative flange 1510. Foil or cap 1508 may be sealed to flange 1510. FIG. 16 shows that sleeve 1502 may include base 1512.

FIG. 17 shows another view of envelope 1500.

Figure 18:
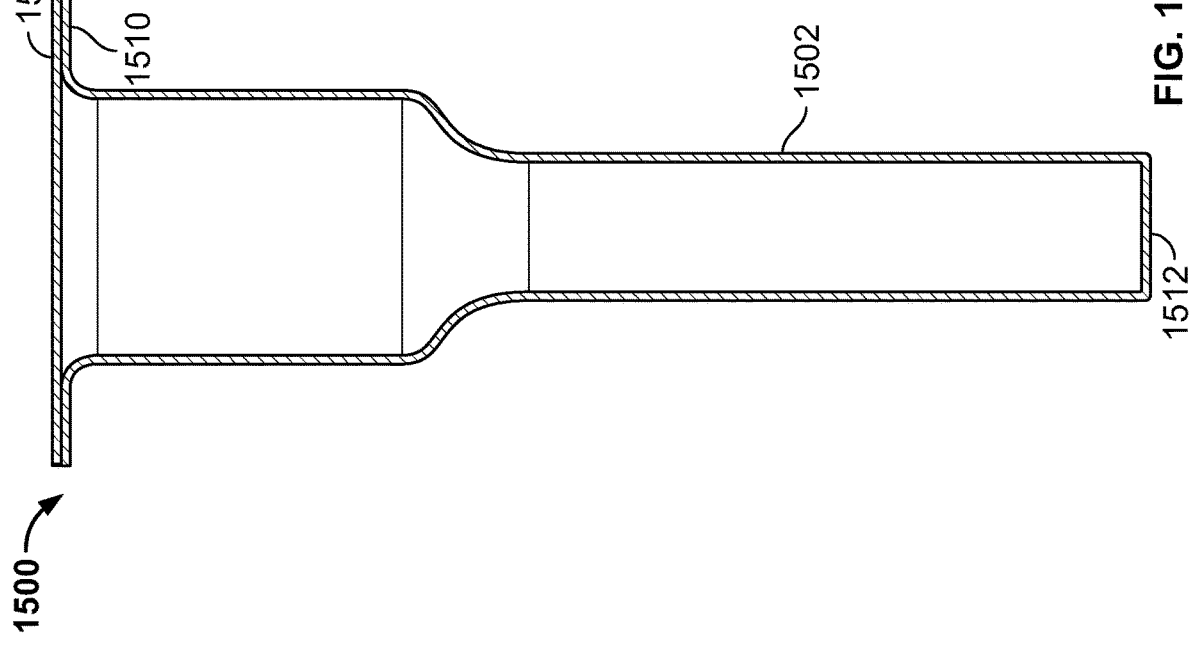
FIG. 18 shows a partial cross-sectional view of apparatus shown in FIG. 17, the view taken along lines 18-18 (shown in FIG. 17)

FIG. 18 shows a cross-sectional view of envelope 1500 taken along lines 18-18 (shown in FIG. 17). Foil or cap 1508 is shown abutting flange 1510.

Figure 19:
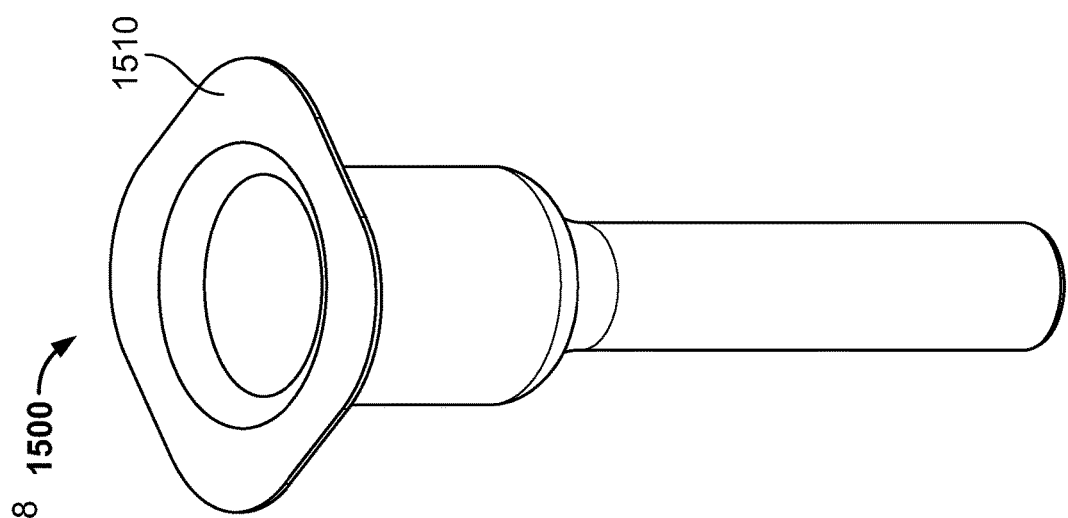
FIG. 19 shows a perspective view of apparatus shown in FIG. 15, in a state different from that shown in FIG. 15.

FIG. 19 shows envelope 1500 without a foil or a cap. An upper surface of flange 1510 is exposed.

Figure 20:
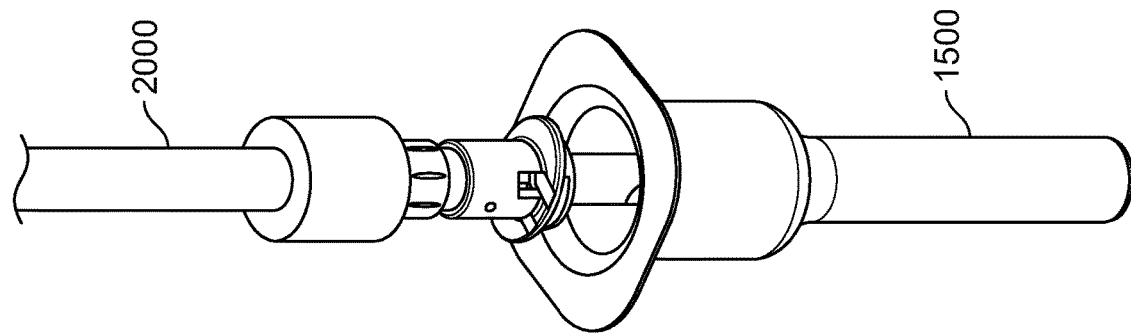
FIG. 20 shows a perspective view of illustrative apparatus in accordance with principles of the invention, including apparatus shown in FIG. 19.

FIG. 20 shows illustrative manipulator arm 2000 (shown in part) delivering apparatus 1200 (shown in FIG. 12) to envelope 1500. The manipulator arm may deliver an apparatus such as apparatus 1000 (shown in FIG. 10), or any other suitable apparatus, to envelope 1500, or any other suitable envelope. The apparatus may be in a non-sterile state. The apparatus may include a medicament (not shown) such as medicament 1260 (shown in FIG. 12), or any other suitable medicament. The apparatus may include a chamber. The chamber may contain the medicament may be in a sterile state. The chamber may be in a sterile state. The medicament may be in a sterile state.

Figures 21, 22:
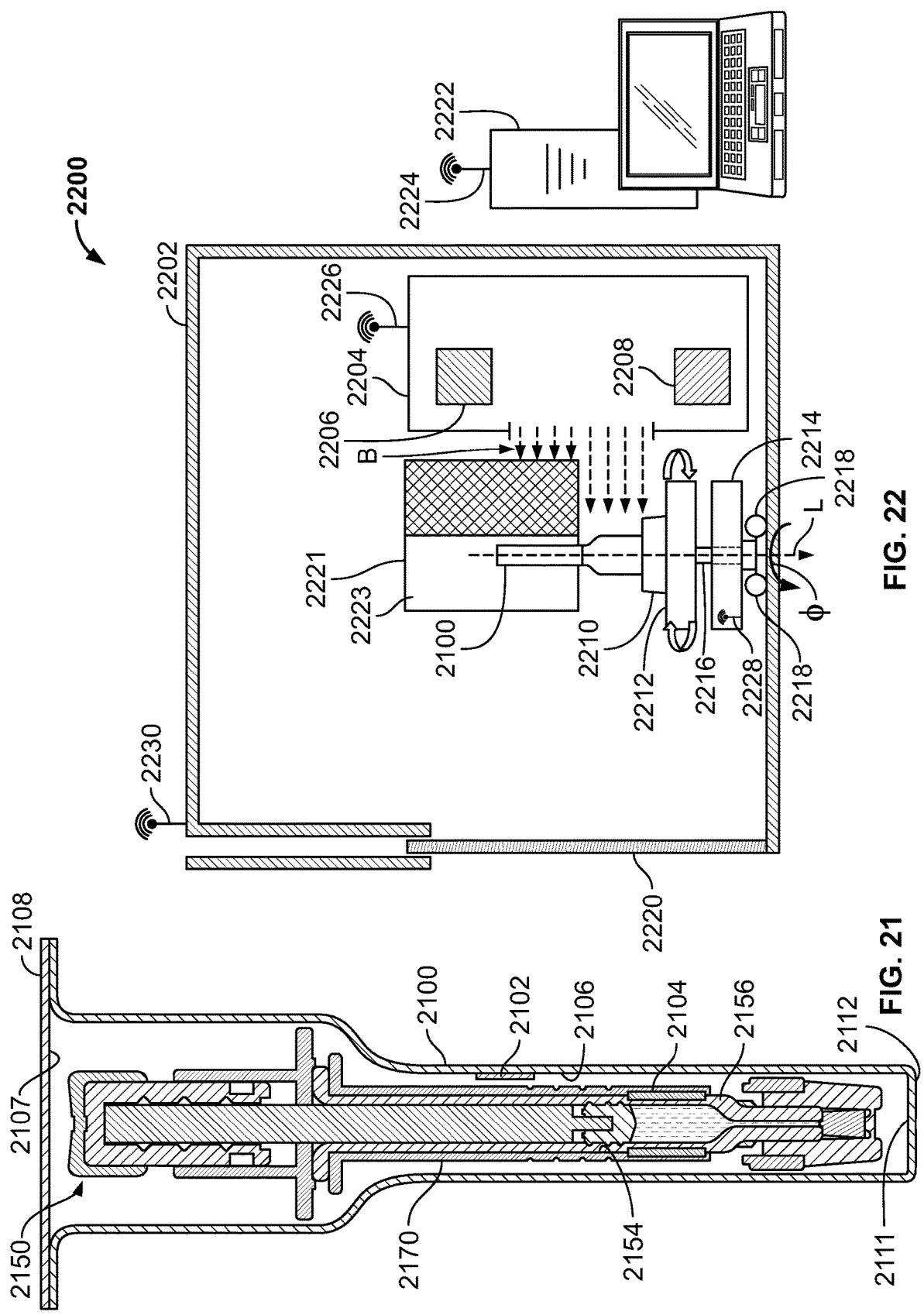
FIG. 21 shows a cross-sectional view of apparatus in accordance with principles of the invention.
FIG. 22 shows a representation of illustrative apparatus in accordance with principles of the invention, including apparatus shown in FIG. 21.

FIG. 21 shows illustrative envelope 2100 and illustrative apparatus 2150. Envelope 2100 may have one or more features in common with envelope 1500 (shown in FIG. 15). Apparatus 2150 may have one or more features in common with one or both of apparatus 1000 (shown in FIG. 10) and apparatus 1200 (shown in FIG. 12).

Apparatus 2150 may be sealed within envelope 2100.

Envelope 2100 may include energy detector 2102. Energy detector 2102 may detect an energy beam such as beam B. Energy detector 2102 may indicate that it has been subjected to an energy beam such as beam B. The indicator may be a visual indicator, such as a color change. The indicator may include a radiochromic dye. The indicator may include a X-ray film. The indicator may be a radio-frequency indicator, such as a radio frequency identification antenna. Energy detector 2102 is shown affixed to inner wall 2106 of envelope 2100. Energy detector 2102 may be disposed on inner surface 2107 of foil or cap 2108, on inner surface 2111 of base 2112, or in any other suitable location in or on envelope 2100, within the structure of the wall of envelope 2100, or within foil or cap 2108.

Apparatus 2150 may include energy detector 2104. Energy detector 2104 may have one or more features in common with energy detector 2102. Energy detector 2104 is shown on outer surface 2154 of chamber 2156, interior to housing 2170. Energy detector 2104 may be disposed on any surface of apparatus 2150, or within the any element of apparatus 2150.

An apparatus such as apparatus 1000 (shown in FIG. 10), or any other suitable apparatus, may be sealed within an envelope such as 1500 (shown in FIG. 15) or any other suitable envelope.

FIG. 22 shows envelope 2100, with apparatus 2150 (shown in FIG. 21) sealed inside, disposed within illustrative sterilization system 2200. Sterilization system 2200 may include an enclosure, such as shielded cabinet 2202. System 2200 may include source 2204 of energy beam B. Source 2204 and envelope 2100 may be arranged such that energy beam B is oriented, relative to apparatus 2150, at an angle to the orientation shown. For example, energy beam B may be oriented parallel to axis L of apparatus 2150. Energy beam B may be oriented obliquely to axis L of apparatus 2150. When energy beam B is oriented parallel to axis L, apparatus 2150 may be arranged such that energy beam B is incident at an end of apparatus 2150 at which the delivery assembly is disposed. When energy beam B is oriented parallel to axis L, apparatus 2150 may be arranged such that energy beam B is incident at an end of apparatus 2150 opposite the end at which the delivery assembly is disposed. System 2200 may include one or more coils 2206 and 2208 for electromagnetically steering focusing beam B. System 2200 may include one or more coils for electromagnetically focusing beam B. Shielded cabinet 2202 may include materials and may be dimensioned to contain beam B, and radiation caused thereby.

System 2200 may include handling robot 2210. Envelope 2100 is shown supported on platen or turret 2212 of robot 2210. Transmission box 2214 may include appropriate power supply and drive mechanisms to rotate shaft 2216. Transmission box 2214 may include appropriate power supply and drive mechanisms to rotate shaft 2216 continuously about axis L. Transmission box 2214 may include appropriate power supply, control and drive mechanisms to rotate shaft 2216 to one or more set values of angle ϕ about axis L. Platen or turret 2212 may rotate with rotation of shaft 2216. Envelope 2210 may rotate with rotation of platen or turret 2212.

Transmission box 2214 may include appropriate power supply, control and drive mechanisms to drive wheels 2218. Wheels 2218 may run along a track (not shown). Wheels 2218 may be steerable and independent of a track.

Shielded cabinet 2202 may include access door 2220.

Shielded cabinet 2202 may include radiation shield 2221. Shield 2221 may shield a portion of envelope 2100. The portion may be less than the entirety of envelope 2100. Shield 2221 may shield a portion of apparatus 2150 (shown in FIG. 21). The portion may be less than the entirety of apparatus 2150. Shield 2221 may be positioned to attenuate energy from beam B that would otherwise impinge on the medicament. Shield 2221 may include slot 2223.

Robot 2210 may move package 2100 into slot 2223 Robot 2210 may move package 2100 into slot 2223 from a side of shield 2221 opposite source 2204. Robot 2210 may move envelope 2100 along slot 2223. Shield 2221 may be lowered about all or part of envelope 2100 after robot 2210 positions envelope 2100 in a path that beam B will follow.

System 2200 may include control hardware 2222. System 2200 may include one or more antennae such as antennae 2224, 2226, 2228 and 2230 for transmission and receipt of signals between the components of system 2200.

Figure 23:
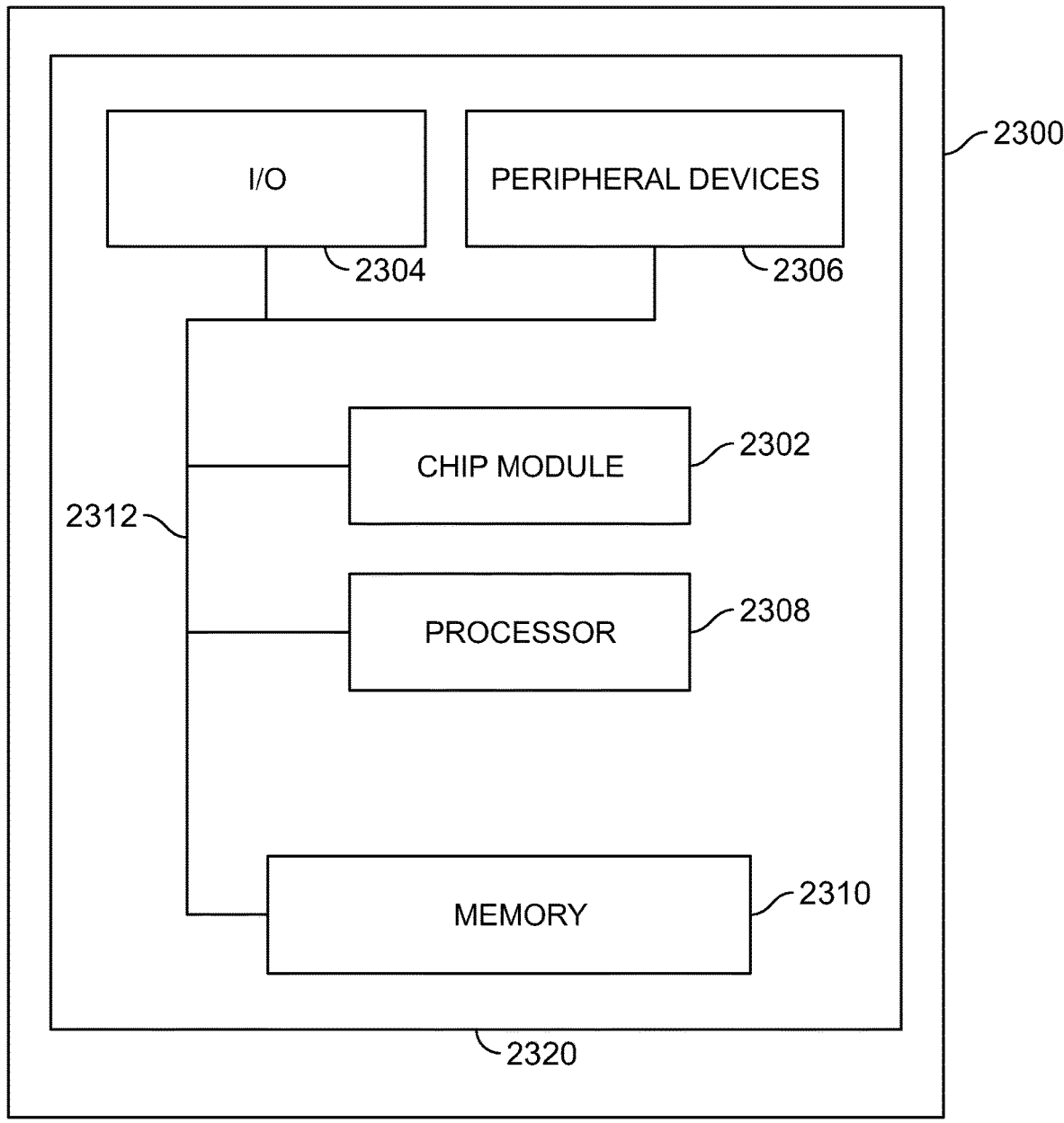
FIG. 23 shows a schematic representation of apparatus that may be configured in accordance with the principles of the invention.

FIG. 23 shows illustrative hardware 2300. Hardware 2300 may be a computing machine. Hardware 2300 may include chip module 2302, which may include one or more integrated circuits, and which may include logic configured to control a robotic sterilization system or to perform any other suitable logical operations.

Hardware 2300 may include one or more of the following components: I/O circuitry 2304, which may include the transmitter device and the receiver device and may interface with fiber optic cable, coaxial cable, telephone lines, wireless devices, PHY layer hardware, a keypad/display control device or any other suitable media or devices; peripheral devices 2306, which may include counter timers, real-time timers, power-on reset generators or any other suitable peripheral devices; logical processing device 2308; and machine-readable memory 2310.

Machine-readable memory 2310 may be configured to store information in machine-readable data-structures.

Components 2302, 2304, 2306, 2308 and 2310 may be coupled together by a system bus or other interconnections 2312 and may be present on one or more circuit boards such as 2320. In some embodiments, the components may be integrated into a single silicon-based chip.

It will be appreciated that software components including programs and data may, if desired, be implemented in ROM (read only memory) form, including CD-ROMs, EPROMs and EEPROMs, or may be stored in any other suitable computer-readable medium such as but not limited to discs of various kinds, cards of various kinds and RAMS. Components described herein as software may, alternatively and/or additionally, be implemented wholly or partly in hardware, if desired, using conventional techniques.

Various signals representing information described herein may be transferred between a source and a destination in the form of electromagnetic waves traveling through signal-conducting media such as metal wires, optical fibers, and/or wireless transmission media (e.g., air and/or space).

Hardware 2300 may operate in a networked environment supporting connections to one or more remote computers via a local area network (LAN), a wide area network (WAN), or other suitable networks. When used in a LAN networking environment, hardware 2300 may be connected to the LAN through a network interface or adapter in I/O circuitry 2304. When used in a WAN networking environment, hardware 2300 may include a modem or other means for establishing communications over the WAN. It will be appreciated that the network connections shown are illustrative and other means of establishing a communications link between the computers may be used. The existence of any of various well-known protocols such as TCP/IP, Ethernet, FTP, HTTP and the like is presumed, and the system may be operated in a client-server configuration to permit a user to operate logical processing device 2308, for example over the Internet.

Hardware 2300 may be included in numerous general purpose or special purpose computing system environments or configurations. Examples of well-known computing systems, environments, and/or configurations that may be suitable for use with the invention include, but are not limited to, personal computers, server computers, hand-held or laptop devices, mobile phones and/or other personal digital assistants ("PDAs"), multiprocessor systems, microprocessor-based systems, tablets, programmable consumer electronics, network personal computers, minicomputers, mainframe computers, distributed computing environments that include any of the above systems or devices, and the like.

Processes in accordance with the principles of the invention may include one or more features of processes illustrated in FIGS. 24-27. The processes may operate on all or some of one or more apparatus such as one or more of the apparatus shown and described above. The processes may operate on all or some of one or more envelope such as one or more of the envelopes shown and described above. For the purpose of illustrating the processes, an apparatus, in whole or in part, in an envelope, in whole or in part, will be referred to as a "package." The system may be implemented using the system of FIG. 22. Operation of the system may be governed by control hardware, such as control hardware 2222 (shown in FIG. 22), which may include the hardware shown in FIG. 23, along with appropriate software.

The steps of the processes may be performed in an order other than the order shown and described herein. Some embodiments of the invention may omit steps shown and described in connection with the illustrative methods. Some embodiments of the invention may include steps that are not shown and described in connection with the illustrative methods.

Figure 24:
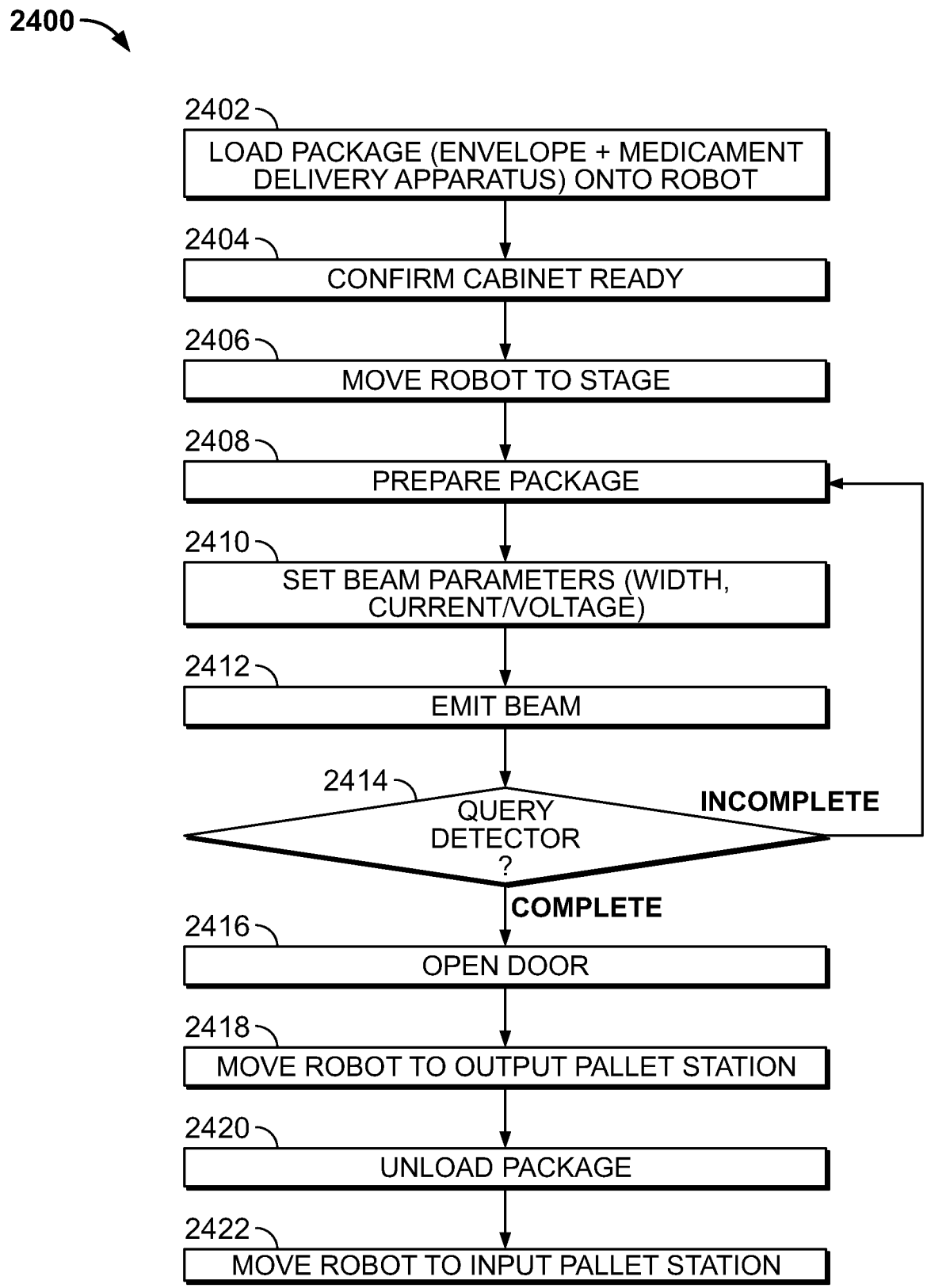
FIG. 24 shows a flow diagram of illustrative process steps in accordance with the principles of the invention.

FIG. 24 shows illustrative process 2400. Process 2400 may begin at step 2402. At step 2402, the system may load a package onto a robot such as robot 2210 (shown in FIG. 22).

At step 2404, the system may confirm that an enclosure, such as cabinet 2202 (shown in FIG. 22) is ready to receive the package.

At step 2406, the system may transmit to the robot an instruction to move into the cabinet.

At step 2408, the system may prepare the package for exposure to an energy beam, such as beam B (shown in FIG. 22).

At step 2410, the system may set beam parameters. The parameters may include one or more of beam width, source current, source voltage, beam pulse duration, beam pulse frequency, beam pulse train duration, beam rasterization width, beam rasterization rate or any other suitable parameters.

At step 2412, the system may emit the beam.

At step 2414, the system may query a radiation detector, such as detector 2104 (shown in FIG. 21). The query may include an optical probe of a radiochromic dye. The system may determine whether the radiation impinged on the detector. The system may determine to what extent the radiation impinged on the detector. The system may compare the extent of impingement to a target dose that is required to satisfy a sterilization requirement.

If at step 2414, the system determines that sterilization is incomplete, process 2400 may continue at step 2408.

If at step 2414, the system determines that sterilization is complete, process 2400 may proceed to step 2416. At step 2416, the system may open a cabinet door, such as door 2220 (shown in FIG. 2200).

At step 2418, the system may instruct the robot to move to an output pallet station.

At step 2420, the system may transfer the package from the robot to a pallet or other container.

At step 2422, the system may instruct the robot to move from the output pallet station to an input pallet station. There, the system may load a different package onto the robot. The different package may be an unsterilized package. The different package may be a partially sterilized package.

Figure 25:
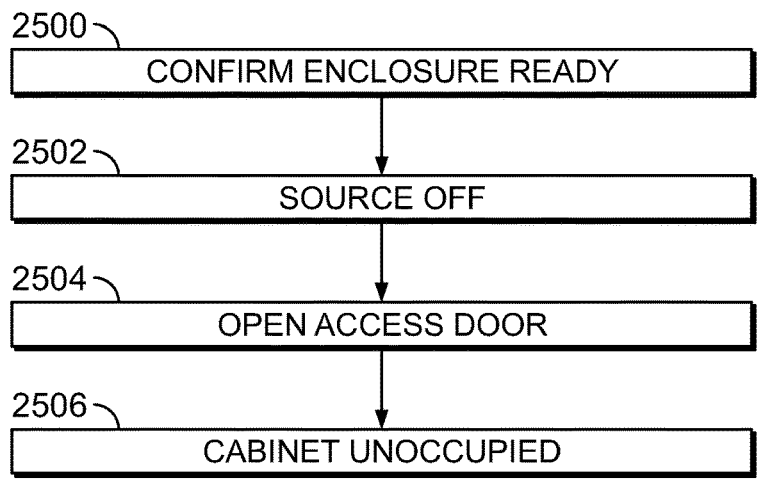
FIG. 25 shows a flow diagram of illustrative process steps in accordance with the principles of the invention.

FIG. 25 shows illustrative process 2500. The system may execute one or more of the steps of process 2500 in connection with the execution of step 2404 of process 2400 (shown in FIG. 24).

Process 2500 may begin at step 2502. At step 2502, the system may turn off a source, such as source 2204 (shown in FIG. 22).

At step 2504, the system may open an access door, such as access door 2220 (shown in FIG. 22).

At step 2506, the system may confirm that the cabinet is unoccupied.

Figure 26:
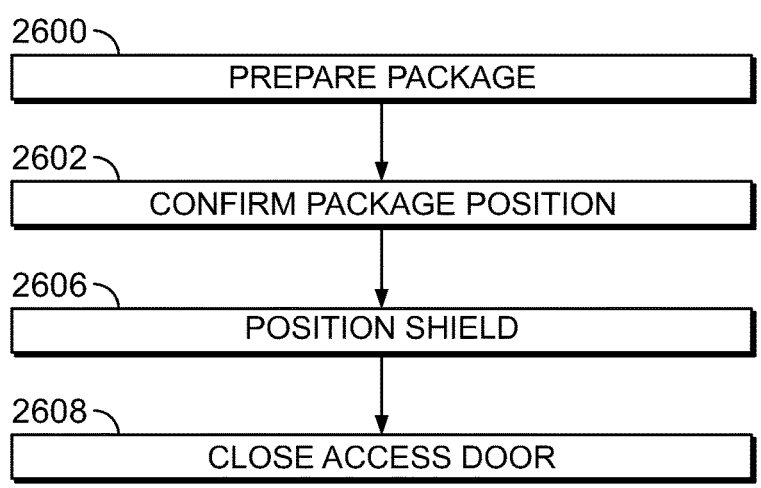
FIG. 26 shows a flow diagram of illustrative process steps in accordance with the principles of the invention.

FIG. 26 shows illustrative process 2600. The system may execute one or more of the steps of process 2600 in connection with the execution of step 2408 of process 2400 (shown in FIG. 24).

Process 2600 may begin at step 2602. At step 2602, the system may confirm the position, relative to beam B, of the package. The position may be confirmed using one or more sensors, such as an optical sensor or any other suitable sensor. The robot may adjust the package position horizontally or vertically.

At step 2606, the system may position one or more radiation shields to shield some or all of the package from beam B or other radiation, such as Bremsstrahlung radiation, that may be present in the cabinet.

At step 2608, the system may close the access door.

Figure 27:
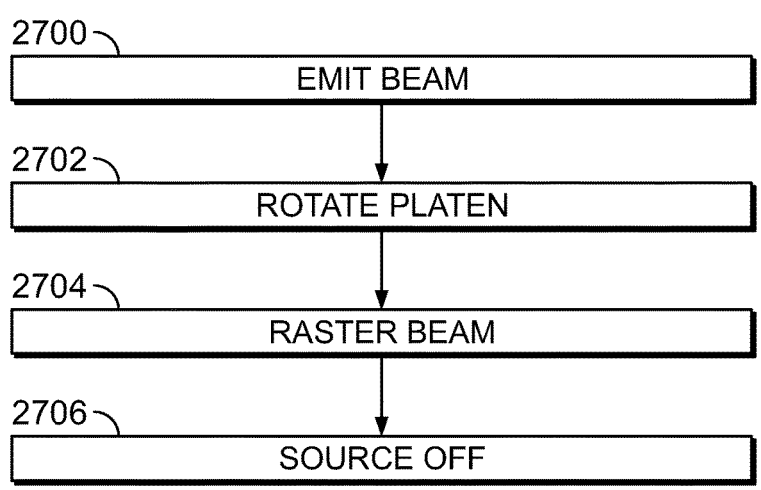
FIG. 27 shows a flow diagram of illustrative process steps in accordance with the principles of the invention.

FIG. 27 shows illustrative process 2700. The system may execute one or more of the steps of process 2700 in connection with the execution of step 2412 of process 2400 (shown in FIG. 24).

Process 2700 may begin at step 2702. At step 2702, the system may instruct the robot to sweep the package relative to beam B through angle $\phi$ (shown in FIG. 22). The system may instruct the robot to rotate the package between two different values of $\phi$.

At step 2704, the system may raster beam B along longitudinal axis L (shown in FIG. 22) of the package. The rasterizing may be synchronized with sweeping so that the region of the package that is exposed to beam B moves longitudinally, circumferentially, or both.

At step 2706, the system may turn off the source.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more (e.g., 1 to 6.1), and ending with a maximum value of 10 or less (e.g., 2.3 to 9.4, 3 to 8, 4 to 7), and to each number 1, 2, 3, 4, 5, 6, 7, 8, 9, and 10 contained within the range.

Thus, apparatus and methods for delivering medicament to a patient have been provided. Persons skilled in the art will appreciate that the present invention can be practiced by other than the described embodiments, which are presented for purposes of illustration rather than of limitation. The present invention is limited only by the claims that follow.

What is claimed is:
1. A medicament delivery apparatus comprising:
 a chamber containing a medicament, and having a medicament delivery outlet and a first electron beam attenuation capacity;
 a delivery assembly having a second electron beam attenuation capacity and including:

a chassis that is fixed, relative to the outlet, to the chamber; and a fluid-displacement member that is configured to move relative to the outlet to move the medicament through the outlet; and an envelope that:

sterilely surrounds the chassis; and encloses no residue from chemical sterilization;

wherein the first electron beam attenuation capacity and the second electron beam attenuation capacity are different.

2. The apparatus of claim 1 wherein the fluid-displacement member comprises a piston.

3. The apparatus of claim 1 wherein the fluid-displacement member comprises a flap.

4. The apparatus of claim 1 wherein the fluid-displacement member comprises an elastic energy storage device.

5. The apparatus of claim 1 wherein the fluid-displacement member comprises a permanent magnet.

6. The apparatus of claim 1 wherein the fluid-displacement member comprises an electromagnet.

7. The apparatus of claim 1 wherein the fluid-displacement member comprises a membrane.

8. The apparatus of claim 7 wherein the membrane is expandable.

9. The apparatus of claim 1 wherein the chamber is included in a barrel of a prefilled syringe.

10. The apparatus of claim 9 wherein the barrel includes glass.

11. The apparatus of claim 9 wherein the barrel includes polymer.

12. The apparatus of claim 9 wherein:

the delivery assembly includes an autoinjector; and the chamber includes a reservoir of the autoinjector.

13. The apparatus of claim 12 wherein the barrel includes glass.

14. The apparatus of claim 12 wherein the barrel includes polymer.

15. The apparatus of claim 9 further comprising, about the medicament and the barrel, a sheath having a third electron beam attenuation capacity that is 10 times smaller than the first electron beam attenuation capacity.

16. The apparatus of claim 1 wherein:

the outlet has a central axis that extends away from the chamber; and the delivery assembly is not rotationally symmetric about the central axis.

17. The apparatus of claim 1 wherein the medicament includes a molecule that has a mass that is not greater than 3,000 Dalton.

18. The apparatus of claim 1 wherein the medicament includes a molecule that has a mass that is not less than 3,000 Dalton and not more than 500,000 Dalton.

19. The apparatus of claim 1 wherein the medicament includes a molecule that has a mass that is not less than 500,000 Dalton.

20. The apparatus of claim 1 wherein the medicament includes a protein.

21. The apparatus of claim 1 wherein the medicament includes a sugar.

22. The apparatus of claim 21 wherein the sugar has a molecular weight that is about 342 gram/mol.

23. The apparatus of claim 1 wherein the medicament includes an antibody.

24. The apparatus of claim 23 wherein the antibody is a monoclonal antibody.

25. The apparatus of claim 1 wherein the medicament includes an antibody fragment.

26. The apparatus of claim 1 wherein the medicament includes a biological product.

27. The apparatus of claim 26 wherein the biological product includes a vaccine.

28. The apparatus of claim 26 wherein the biological product includes a blood element.

29. The apparatus of claim 26 wherein the biological product includes blood.

30. The apparatus of claim 26 wherein the biological product includes an allergenic.

31. The apparatus of claim 26 wherein the biological product includes a cell.

32. The apparatus of claim 31 wherein the cell is alive.

33. The apparatus of claim 26 wherein the biological product includes a gene.

34. The apparatus of claim 26 wherein the biological product includes tissue.

35. The apparatus of claim 34 wherein the tissue is alive.

36. The apparatus of claim 26 wherein the biological product includes a nucleic acid.

37. The apparatus of claim 26 wherein the biological product includes a peptide therapeutic.

38. The apparatus of claim 1 wherein the envelope includes a sleeve.

39. The apparatus of claim 1 wherein the envelope includes a radiation detector.

40. The apparatus of claim 1 wherein the envelope includes an atmosphere that is enriched, relative to an atmosphere exterior and adjacent to the envelope, in an inert gas.

41. The apparatus of claim 40 wherein the inert gas comprises nitrogen, $N_2$.

42. The apparatus of claim 1 further comprising a water-absorbing compound that is enclosed inside the envelope at a concentration that is greater than a concentration of the compound in an atmosphere exterior and adjacent to the envelope.

43. The apparatus of claim 1 wherein a concentration of gaseous oxygen, $O_2$, enclosed in the envelope, is no greater than 1 part per million.

44. The apparatus of claim 1 wherein a concentration of gaseous water vapor, $H_2O$, enclosed in the envelope, is no greater than 1 part per million.

45. The apparatus of claim 1 wherein the envelope includes:

a first impermeable member that is impermeable to mass transfer; and, opposite the first impermeable member, a second impermeable member that is impermeable to mass transfer, the first and second impermeable members being sealed to each other.

46. The apparatus of claim 45 wherein the first impermeable member is recessed to accommodate the delivery assembly.

47. The apparatus of claim 46 wherein the first impermeable member comprises a molded polymer.

48. The apparatus of claim 45 wherein the second impermeable member includes a foil.

49. The apparatus of claim 48 wherein the foil comprises polyethylene.

50. The apparatus of claim 45 wherein:

the first impermeable member includes a foil; and the second impermeable member includes a foil.

51. The apparatus of claim 45 wherein:

the first impermeable member is recessed to accommodate the delivery assembly; and the second impermeable member is recessed to accommodate the delivery assembly.

52. The apparatus of claim 45 wherein:
the first impermeable member includes a sheath; and
the second impermeable member includes a cap.

53. The apparatus of claim 52 wherein the cap comprises a foil.

54. The apparatus of claim 1 wherein the envelope includes a blister pack.

55. The apparatus of claim 1 wherein the residue includes a vapor.

56. The apparatus of claim 1 wherein the residue includes an adsorbed molecule.

57. The apparatus of claim 56 wherein the adsorbed molecule is disposed on the envelope.

58. The apparatus of claim 56 wherein none of the residue is disposed on the delivery assembly.

59. The apparatus of claim 1 wherein the first electron beam attenuation capacity is greater than the second electron beam attenuation capacity by a multiple that is greater than 1.

60. The apparatus of claim 1 wherein the envelope has a third electron beam attenuation capacity that is 50 times smaller than the first electron beam attenuation capacity.

61. The apparatus of claim 1 wherein the delivery assembly includes:
a toroidal element disposed about a longitudinal axis; and
a shaft disposed along the longitudinal axis.

62. The apparatus of claim 61 wherein the toroidal element is rotatable, about the longitudinal axis, relative to the shaft.

63. A medicament delivery apparatus comprising:
a chamber containing a medicament, and having a medicament delivery outlet and a first X-ray beam attenuation capacity;
a delivery assembly having a second X-ray beam attenuation capacity and including:
a chassis that is fixed, relative to the outlet, to the chamber; and
a fluid-displacement member that is configured to move relative to the outlet to move the medicament through the outlet; and
an envelope that:
sterilely surrounds the chassis; and
encloses no residue from chemical sterilization;
wherein the first X-ray beam attenuation capacity and the second X-ray beam attenuation capacity are different.

64. The apparatus of claim 63 wherein the fluid-displacement member comprises a piston.

65. The apparatus of claim 63 wherein the fluid-displacement member comprises a flap.

66. The apparatus of claim 63 wherein the fluid-displacement member comprises an elastic energy storage device.

67. The apparatus of claim 63 wherein the fluid-displacement member comprises a permanent magnet.

68. The apparatus of claim 63 wherein the fluid-displacement member comprises an electromagnet.

69. The apparatus of claim 63 wherein the fluid-displacement member comprises a membrane.

70. The apparatus of claim 69 wherein the membrane is expandable.

71. The apparatus of claim 63 wherein the chamber is included in a barrel of a prefilled syringe.

72. The apparatus of claim 71 wherein the barrel includes glass.

73. The apparatus of claim 71 wherein the barrel includes polymer.

74. The apparatus of claim 71 wherein:
the delivery assembly includes an autoinjector; and
the chamber includes a reservoir of the autoinjector.

75. The apparatus of claim 74 wherein the barrel includes glass.

76. The apparatus of claim 74 wherein the barrel includes polymer.

77. The apparatus of claim 71 further comprising, about the medicament and the barrel, a sheath having a third X-ray beam attenuation capacity that is 10 times smaller than the first X-ray beam attenuation capacity.

78. The apparatus of claim 63 wherein:
the outlet has a central axis that extends away from the chamber; and
the delivery assembly is not rotationally symmetric about the central axis.

79. The apparatus of claim 63 wherein the medicament includes a molecule that has a mass that is not greater than 3,000 Dalton.

80. The apparatus of claim 63 wherein the medicament includes a molecule that has a mass that is not less than 3,000 Dalton and not more than 500,000 Dalton.

81. The apparatus of claim 63 wherein the medicament includes a molecule that has a mass that is not less than 500,000 Dalton.

82. The apparatus of claim 63 wherein the medicament includes a protein.

83. The apparatus of claim 63 wherein the medicament includes a sugar.

84. The apparatus of claim 83 wherein the sugar has a molecular weight that is about 342 gram/mol.

85. The apparatus of claim 63 wherein the medicament includes an antibody.

86. The apparatus of claim 85 wherein the antibody is a monoclonal antibody.

87. The apparatus of claim 63 wherein the medicament includes an antibody fragment.

88. The apparatus of claim 63 wherein the medicament includes a biological product.

89. The apparatus of claim 88 wherein the biological product includes a vaccine.

90. The apparatus of claim 88 wherein the biological product includes a blood element.

91. The apparatus of claim 88 wherein. tle biological product includes blood.

92. The apparatus of claim 88 wherein the biological product includes an allergenic.

93. The apparatus of claim 88 wherein the biological product includes a cell.

94. The apparatus of claim 93 wherein the cell is alive.

95. The apparatus of claim 88 wherein the biological product includes a gene.

96. The apparatus of claim 88 wherein the biological product includes tissue.

97. The apparatus of claim 96 wherein the tissue is alive.

98. The apparatus of claim 88 wherein the biological product includes a nucleic acid.

99. The apparatus of claim 88 wherein the biological product includes a peptide therapeutic.

100. The apparatus of claim 63 wherein the envelope includes a sleeve.

101. The apparatus of claim 63 wherein the envelope includes a radiation detector.

102. The apparatus of claim 63 wherein the envelope includes an atmosphere that is enriched, relative to an atmosphere exterior and adjacent to the envelope, in an inert gas.

103. The apparatus of claim 102 wherein the inert gas comprises nitrogen, $N_2$.

104. The apparatus of claim 63 further comprising a water-absorbing compound that is enclosed inside the envelope at a concentration that is greater than a concentration of the compound in an atmosphere exterior and adjacent to the envelope.

105. The apparatus of claim 63 wherein a concentration of gaseous oxygen, $O_2$, enclosed in the envelope, is no greater than 1 part per million.

106. The apparatus of claim 63 wherein a concentration of gaseous water vapor, $H_2O$, enclosed in the envelope, is no greater than 1 part per million.

107. The apparatus of claim 63 wherein the envelope includes:
   a first impermeable member that is impermeable to mass transfer; and,
   opposite the first impermeable member, a second impermeable member that is impermeable to mass transfer, the first and second impermeable members being sealed to each other.

108. The apparatus of claim 107 wherein the first impermeable member is recessed to accommodate the delivery assembly.

109. The apparatus of claim 108 wherein the first impermeable member comprises a molded polymer.

110. The apparatus of claim 107 wherein the second impermeable member includes a foil.

111. The apparatus of claim 110 wherein the foil comprises polyethylene.

112. The apparatus of claim 107 wherein:
   the first impermeable member includes a foil; and
   the second impermeable member includes a foil.

113. The apparatus of claim 107 wherein:
   the first impermeable member is recessed to accommodate the delivery assembly; and
   the second impermeable member is recessed to accommodate the delivery assembly.

114. The apparatus of claim 107 wherein:
   the first impermeable member includes a sheath; and
   the second impermeable member includes a cap.

115. The apparatus of claim 114 wherein the cap comprises a foil.

116. The apparatus of claim 63 wherein the envelope includes a blister pack.

117. The apparatus of claim 63 wherein the residue includes a vapor.

118. The apparatus of claim 63 wherein the residue includes an adsorbed molecule.

119. The apparatus of claim 118 wherein the adsorbed molecule is disposed on the envelope.

120. The apparatus of claim 118 wherein none of the residue is disposed on the delivery assembly.

121. The apparatus of claim 63 wherein the first X-ray beam attenuation capacity is greater than the second X-ray beam attenuation capacity by a multiple that is greater than 1.

122. The apparatus of claim 63 wherein the envelope has a third X-ray beam attenuation capacity that is 50 times smaller than the first X-ray beam attenuation capacity.

123. The apparatus of claim 63 wherein the delivery assembly includes:
   a toroidal element disposed about a longitudinal axis; and
   a shaft disposed along the longitudinal axis.

124. The apparatus of claim 123 wherein the toroidal element is rotatable, about the longitudinal axis, relative to the shaft.

\* \* \* \* \*